(12) United States Patent
Aves et al.

(10) Patent No.: US 6,902,547 B2
(45) Date of Patent: Jun. 7, 2005

(54) MEDICAL NEEDLE

(76) Inventors: Teodulo Aves, 8772 Dallam Ct., Houston, TX (US) 77064-8611; Jeffrey Charnov, 5 Dunnam La., Houston, TX (US) 77024

( * ) Notice: Subject to any disclaimer, the term of this patent is extended or adjusted under 35 U.S.C. 154(b) by 0 days.

(21) Appl. No.: 09/994,320

(22) Filed: Nov. 26, 2001

(65) Prior Publication Data

US 2003/0028147 A1 Feb. 6, 2003

Related U.S. Application Data

(63) Continuation-in-part of application No. 09/921,179, filed on Aug. 2, 2001, now Pat. No. 6,554,809.

(51) Int. Cl.[7] ............................................... A61M 5/32
(52) U.S. Cl. ....................... 604/272; 604/264; 604/500; 606/108
(58) Field of Search ............................... 604/272–274, 604/264, 93.01, 158–160, 164.01–166.01, 74.01, 170.03, 71, 171, 43.48, 523, 524, 22, 500, 506, 507, 508, 510, 268; 606/108, 131, 139, 148, 159, 170, 185, 190, 222, 223

(56) References Cited

U.S. PATENT DOCUMENTS

| 4,141,365 A | * | 2/1979 | Fischell et al. ............. 128/404 |
|---|---|---|---|
| 4,781,691 A | * | 11/1988 | Gross ......................... 604/164 |
| 4,945,895 A | * | 8/1990 | Takai et al. ..................... 128/6 |
| 5,255,691 A | | 10/1993 | Otten .......................... 607/117 |
| 5,433,739 A | | 7/1995 | Sluijter et al. ................ 607/99 |
| 5,730,732 A | * | 3/1998 | Sardelis et al. ............. 604/272 |
| 5,730,754 A | | 3/1998 | Obenchain .................. 606/185 |
| 6,010,493 A | | 1/2000 | Snoke ......................... 604/510 |
| 6,095,149 A | * | 8/2000 | Sharkey et al. ............. 128/898 |
| 6,104,960 A | | 8/2000 | Duysens et al. ............ 607/117 |
| 6,233,488 B1 | | 5/2001 | Hess ............................ 607/58 |
| 6,261,311 B1 | | 7/2001 | Sharkey et al. ............... 607/96 |
| 6,283,948 B1 | * | 9/2001 | McKernan et al. ......... 604/272 |

OTHER PUBLICATIONS

Aves, U.S. Appl. No. 09/921,179 filed Aug. 2, 2001, 29 pages.

* cited by examiner

Primary Examiner—Long V. Le
Assistant Examiner—Ann Y. Lam
(74) Attorney, Agent, or Firm—Osha & May L.L.P.

(57) ABSTRACT

A needle comprising a hollow shaft having opposed distal and proximal ends, the hollow shaft having a lumen extending from the proximal end of the shaft and terminating at an opening on a top of and proximal to the distal end of the needle shaft. A cutting surface is at the distal end of the hollow shaft adapted to be inserted into a patient, wherein the cutting surface is on the bottom of the distal end of the hollow shaft.

21 Claims, 14 Drawing Sheets

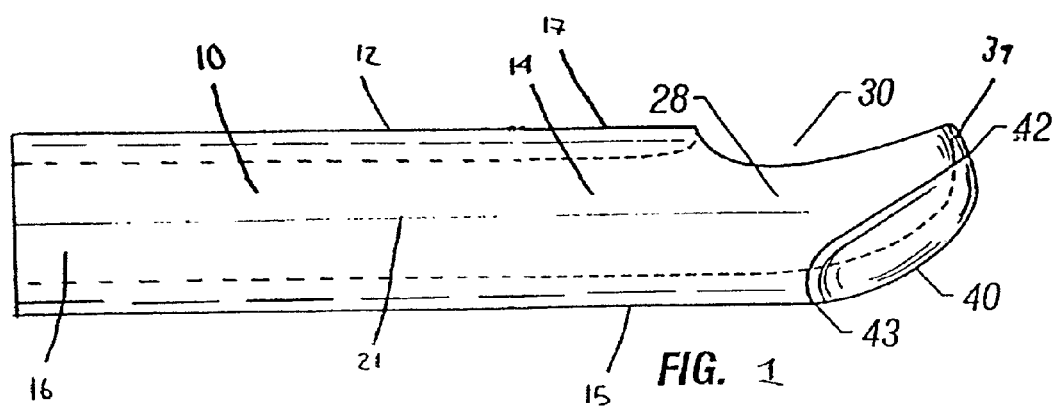

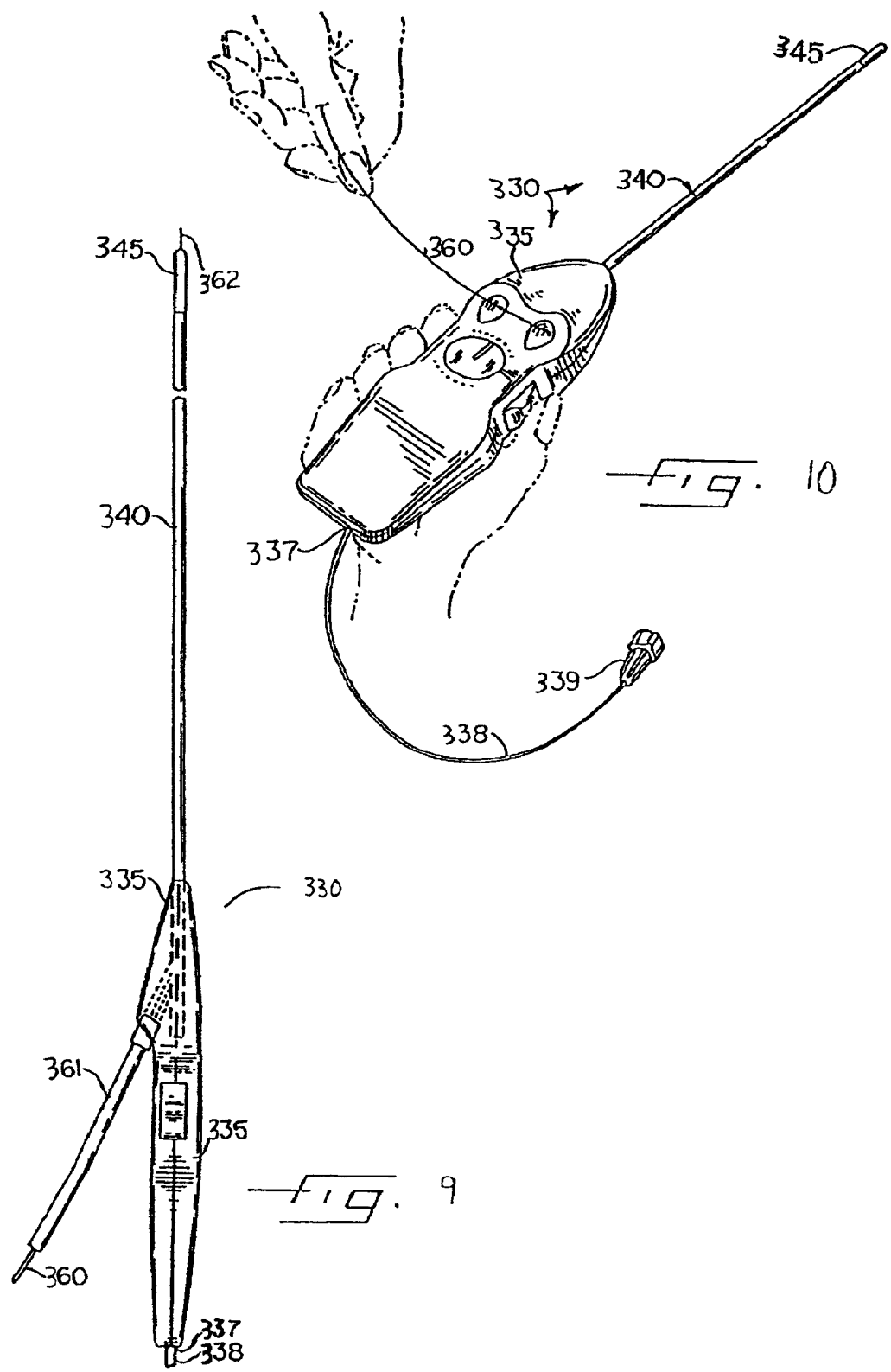

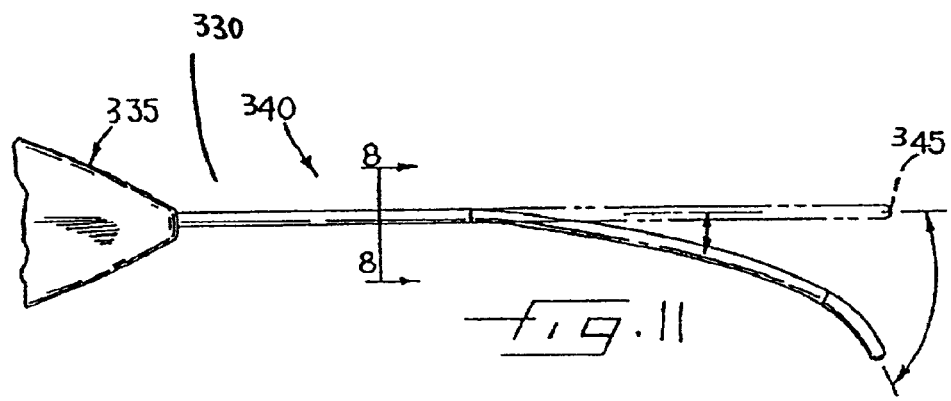
fig. 11
fig. 12
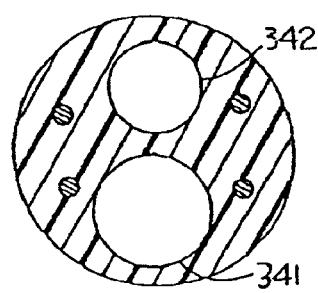
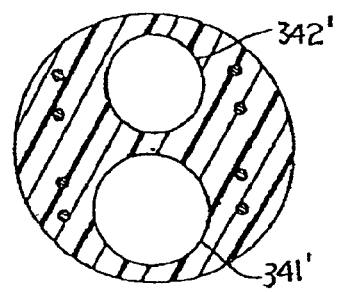
fig. 13
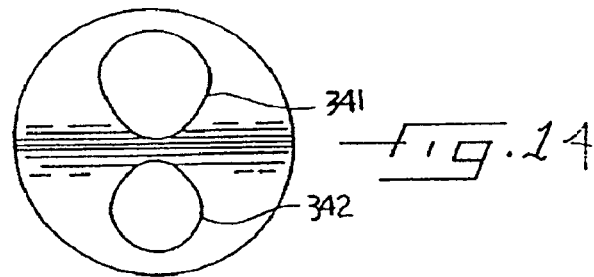
fig. 14
fig. 15
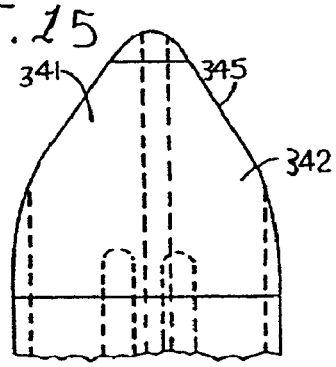
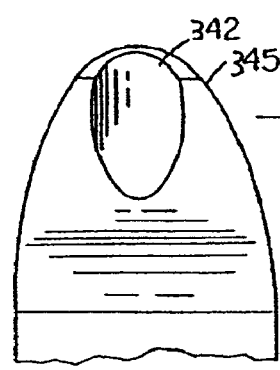
fig. 16

MEDICAL NEEDLE

CROSS-REFERENCE TO RELATED APPLICATIONS

This application claims priority from and is a continuation in part of U.S. application Ser. No. 09/921,179, filed on Aug. 2, 2001 now U.S. Pat. No. 6,554,809.

BACKGROUND OF INVENTION

1. Field of the Invention

The invention relates generally to the field of medical needles and methods of using the same.

2. Background Art

Minimally-invasive medical procedures have had a dramatic increase in popularity. This popularity is partly due to decreased complications from the procedures, a shortened recovery time for the patients, and a lower cost for the procedures. A great deal of new technology has been developed for these minimally-invasive procedures including electrodes, catheters, surgical tools, cameras, lasers, heating and cooling mechanisms, probes, cutting tools, lights, and other types of apparatus that can be passed through the lumen of a needle in order to carry out a variety of procedures.

Copending U.S. application Ser. No. 09/921,179, filed on Aug. 2, 2001, discloses a needle comprising a hollow shaft having opposed distal and proximal ends, the hollow shaft having a lumen extending from the proximal end of the shaft and terminating at an opening on a top of and proximal to the distal end of the needle shaft. A cutting surface is at the distal end of the hollow shaft adapted to be inserted into a patient, wherein the cutting surface is on the bottom of the distal end of the hollow shaft. Copending U.S. application Ser. No. 09/921,179 is incorporated herein by reference in its entirety.

U.S. Pat. No. 4,141,365 discloses a tissue stimulation apparatus for positive positioning of an electrode-bearing lead proximous to tissue which is to be stimulated electrically. The apparatus particularly includes a body penetration and insertion assembly which carries an elongated flexible strip of physiologically inert plastic material having at least one electrode positioned thereon into contacting relation with said tissue. The insertion assembly comprises a hollow needle having a slot formed longitudinally along the length of one wall thereof, the slot allowing transverse removal of the flexible lead from the needle after proper positioning of the lead and after removal of the needle from the body. The slotted assembly allows use of a flexible electrode lead having electrical connections at the external end thereof which are too large to pass through the hollow needle. U.S. Pat. No. 4,141,365 is incorporated herein by reference in its entirety.

U.S. Pat. No. 5,255,691 discloses an improved method and apparatus for introducing a flexible member into the epidural space of the spinal column of a patient employing an introducer assembly for achieving access to the epidural space. The introducer assembly includes an epidural needle assembly, including an elongated needle having a side opening at its distal tip, a hub at its proximal tip and a lumen extending therebetween, and a stylet removable and insertable within the lumen of said needle through said hub and having a beveled tip and a hub. The distal tip may be curved in the direction of the side opening when unrestrained by the stylet. The introducer assembly has a locking mechanism which preferably includes a lug extending from the side of the needle hub and an L-shaped cut-out in the side of the stylet hub for receiving the lug therein and allowing its rotation 90° to effect a bayonette-style locking of the two hubs. U.S. Pat. No. 5,255,691 is incorporated herein by reference in its entirety.

U.S. Pat. No. 5,433,739 discloses a technique of relieving back pain by heating of an intervertebral disc. The heating is illustrated by a percutaneous technique where a needle or electrode is inserted into the disc under X-ray or other imaging control and subsequently used to elevate the temperature of the disc. Above a certain temperature, the innervation related to the disc is destroyed to the point that back pain related to that innervation also can be eliminated. Specific examples of methods and apparatus to achieve such disc heating are given. Among the methods are use of radiofrequency heating and direct current heating, use of stimulation and impedance monitoring to improve target control, and the use of temperature monitoring to determine and quantify the appropriate disc temperature to achieve the desired clinical results. U.S. Pat. No. 5,433,739 is incorporated herein by reference in its entirety.

U.S. Pat. No. 5,730,754 discloses devices and methods for accessing the spinal epidural space via the neural foramen. In one aspect, a deflecting conduit needle device is disclosed having an elongated body extending substantially along a first axis. The device has a proximal end and a distal end, and a transverse conduit, positioned along the distal one-eighth of the device and extending substantially along a second axis, wherein the second axis is positioned at an acute angle relative to the first axis. In another aspect a method is disclosed for accessing the spinal epidural space via the neural foramen. U.S. Pat. No. 5,730,754 is incorporated herein by reference in its entirety.

U.S. Pat. No. 6,010,493 discloses a method of epidural surgery that improves visibility in the epidural space of a patient for more effectively conducting therapeutic surgery therein. The method includes the steps of distending a portion of the epidural space of a patient by filling the portion of the epidural space with a fluid supplied from a catheter and positioning a portion of an optical scope in the distended portion of the epidural space by inserting the optical scope through the same catheter that supplies the distending fluid to thereby provide a visual image of the epidural space. U.S. Pat. No. 6,010,493 is incorporated herein by reference in its entirety.

U.S. Pat. No. 6,104,960 discloses a system and method for providing medical electrical stimulation to a portion of the nervous system. The system includes a rigid hollow needle having a lumen and a flexible lead body disposed within the lumen of the needle, the lead body having an insulated coiled proximal section and an electrode section. The proximal section comprises a conductor which is coiled and insulated, the electrode section comprises a portion of the coiled conductor which is not insulated. In an alternative embodiment, the electrode section features a crimp core around which a distal end of the coiled conductor which is not insulated is crimped, the rigid hollow needle is metal but which is partially covered along its outer surface with an insulation. In still further embodiments, the flexible lead body has a stylet lumen therein and the lead body also has a connector pin for electrically connecting the electrical conductor to a pulse generator. Preferably this connector pin located on a proximal end of the lead body and having a diameter no greater than the inner diameter of the needle. A method of providing temporary electrical stimulation to the sacral nerve is also disclosed. U.S. Pat. No. 6,104,960 is incorporated herein by reference in its entirety.

U.S. Pat. No. 6,233,488 discloses a method for suppressing chemical substance craving that comprises an electrical stimulation of the spinal cord using one or more implantable leads containing at least two conducting electrodes. The method may be used to suppress craving for alcohol, narcotics, cocaine, and amphetamines. The method is particularly suited to the suppression of nicotine craving. U.S. Pat. No. 6,233,488 is incorporated herein by reference in its entirety.

U.S. Pat. No. 6,261,311 discloses a percutaneous method of repairing a fissure in the annulus pulposus that includes placing an energy source adjacent to the fissure and providing sufficient energy to the fissure to raise the temperature to at least about 45–70° C. and for a sufficient time to cause the collagen to fues. An intervertebral fissure also can be treated by placing a catheter with a lumen adjacent to the fissure and injecting sealant into the fissure via the catheter, thereby sealing the fissure. An intervertebral fissure additionally can be treated by providing a catheter having a distal end, a proximal end, a longitudinal axis, and an intradiscal section at the catheter's distal end on which there is at least one functional element. The next step is applying a force longitudinally to the proximal end of the catheter which is sufficient to advance the intradiscal section through the nucleus pulposus and around an inner wall of an annulus fibrosus, but which force is insufficient to puncture the annulus fibrosus. Next the functional element is positioned at a selected location of the disc by advancing or retracting the catheter and optionally twisting the proximal end of the catheter. Then the functional unit treats the annular fissure. Optionally, there is an additional step of adding a substance to seal the fissure. An externally guidable intervertebral disc apparatus also is disclosed. U.S. Pat. No. 6,261,311 is incorporated herein by reference in its entirety.

SUMMARY OF INVENTION

In some embodiments, the invention relates to a needle comprising a hollow shaft having opposed distal and proximal ends, the hollow shaft having a lumen extending from the proximal end of the shaft and terminating at an opening on a top of and proximal to the distal end of the needle shaft. The hollow shaft is adapted to receive an epidural catheter for introducing liquid anesthesia into the patient which can be threaded through the proximal end of the needle until a portion of the catheter exits through the lumen opening on the top of the distal end of the needle shaft; the shaft also has a cutting surface at the distal end of the hollow shaft adapted to be inserted into a patient, wherein the cutting surface is on the bottom of the distal end of the hollow shaft.

In other embodiments, the invention relates to a method of installing a catheter in the epidural space comprising pushing a needle into the epidural space with a cutting surface of the needle substantially parallel to the dura fibers of the patient, wherein the needle comprises a substantially straight cutting surface, feeding a catheter through the needle and into the epidural space, removing the needle while holding the catheter stationary, and securing the catheter.

Advantages of the invention may include one or more of the following:

Providing a needle that avoids inadvertent penetration through the dura mater and into the subarachnoid space, causing spinal fluid to leak out;

Providing a needle that avoids the onset of postdural puncture headache;

Providing a needle that limits the number of dural or other bodily fibers that are cut during use;

Providing a needle that limits damage to the neural fibers in the event of penetration into the spinal cord;

Providing a safer needle;

Providing a needle that has a cutting edge that is parallel to the dural or other bodily fibers; and Providing a needle that has an increased sensitivity to the loss of resistance which can be used for detection of the epidural space.

Other aspects and advantages of the invention will be apparent from the following description and the appended claims.

BRIEF DESCRIPTION OF DRAWINGS

FIG. 1 is a side elevational view, greatly enlarged, illustrating a needle in accordance with an embodiment of the invention;

FIG. 9 is a side elevational view of a catheter having a fiberscope inserted therein according to an embodiment of the present invention;

FIG. 10 is a perspective view of a catheter having a fiberscope inserted therein according to an embodiment of the present invention;

FIG. 11 is fragmentary top elevational view of a catheter according to an embodiment of the present invention;

FIG. 12 is an enlarged cross-sectional view of an embodiment of a catheter taken along line 8—8 of FIG. 11;

FIG. 13 is an enlarged cross-sectional view of an embodiment of a catheter taken along line 8—8 of FIG. 11;

FIG. 14 is an enlarged distal end plan view of a catheter taken from a distal end thereof according to an embodiment of the present invention;

FIG. 15 is an enlarged fragmentary top plan view of a distal end of a catheter having phantom lines therein illustrating the positioning of the multiple lumens within the catheter according to an embodiment of the present invention;

FIG. 16 is enlarged fragmentary side plan view of a distal end of a catheter according to an embodiment of the present invention;

DETAILED DESCRIPTION

Figure 2A:
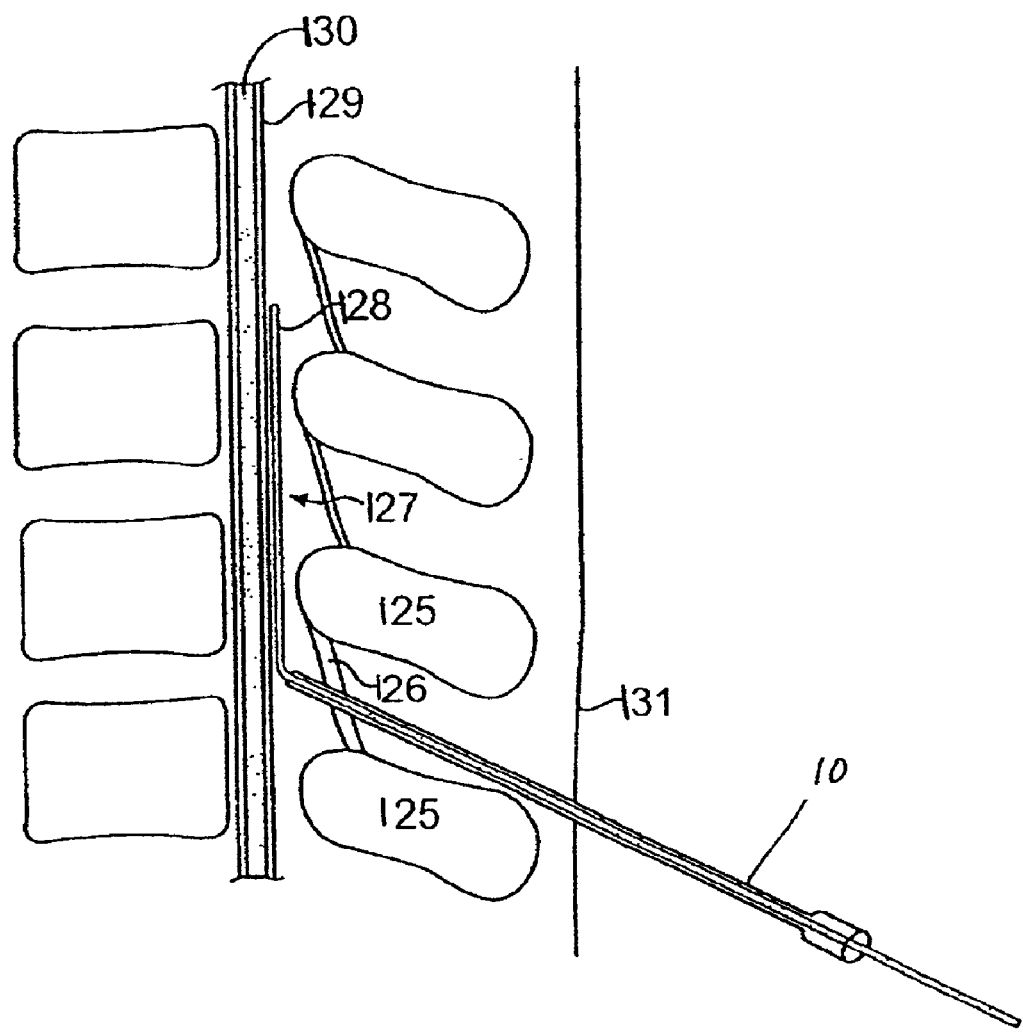
FIGS. 2a and 2b are side views of catheter placement and an anterior posterior view of catheter placement, respectively.

The present invention is directed to straight and curved needles which may be used for minimally-invasive or interventional procedures.

In one embodiment of the invention, the distal end (14) of a needle (10), as seen in FIG. 1, has a top side (17) and a bottom side (15). The cutting surface (40) is located on the bottom side (15), while the opening (30) of the lumen (28) is on the top side (17).

In another embodiment of the invention, the needle (10) has a first lumen (28) and a second lumen (not shown). The first lumen (28) is adapted to be used with a catheter, a stylet, and/or any other medical devices. The first lumen (28) may have an opening (30) on the on the top (17) of the distal end (14) of the needle (10). The second lumen (not shown) may have an opening (not shown) on the bottom (15) of the distal end (14) of the needle (10). In one embodiment, the opening (not shown) of the second lumen is on the beveled surface (39) at the distal end of the needle (10). In another embodiment, the opening (not shown) of the second lumen is adjacent the cutting surface (40) on the bottom side (15) but slightly towards the top (17) of the needle (10), in either direction from the cutting surface (40). The second lumen is adapted to be used with a spinal needle, a pulsating syringe, other known devices to sense a pressure drop in the epidural region, and/or other medical devices.

In another embodiment of the invention, the needle (10) has a lumen (28) having a first opening (30) on the top (17) of the distal end of the needle (10) and a second opening (not shown) on the bottom (15) of the distal end of the needle (10). In one embodiment, the second opening (not shown) of lumen (28) is on the beveled surface (39) at the distal end of the needle (10). In another embodiment, the second opening (not shown) of the lumen (28) is adjacent the cutting surface (40) on the bottom side (15), but slightly towards the top (17) of the needle (10), in either direction from the cutting surface (40). In one embodiment, the second opening may be angled away from an axis (21) of the shaft of the needle (12) in order to reduce the incidence of plugging. The second opening is adapted to be used with a spinal needle, a pulsating syringe, other devices to sense a pressure drop in the epidural region, and/or other medical devices. The first opening (30) is adapted to be used with a catheter, a stylet, and/or any other medical devices. The first opening (30) may be on the on the top of the distal end (14) of the needle (10).

In one embodiment, the needle may be provided with a solid or, optionally, semi-rigid plastic stylet (not shown) which may be inserted into the lumen (28) at the proximal end (16) of the needle (10) and may extend to the opening (30) at the distal end of the lumen (28). The stylet performs the function with the needle (10) of preventing body tissue from blocking or clogging the lumen (28) during penetration of the needle through the tissue of the patient. After the needle has penetrated the tissue, the stylet has served its function and then may be removed, by grasping the proximal end of the stylet or a handle of the stylet and retracting.

One embodiment of the present invention has a cutting surface (40) at the distal end (14) of the needle (10). In one embodiment, the cutting surface (40) may be between parallel and perpendicular to the longitudinal axis (21) of the needle shaft (12); in another embodiment the cutting surface (40) is at an angle of about 10° to about 80° to the longitudinal axis (21) of the needle shaft (12). In another embodiment the cutting surface (40) is at an angle of about 20° to about 60° to the longitudinal axis (21) of the needle shaft (12); and in another embodiment the cutting surface (40) is at an angle of about 30° to about 45° to the longitudinal axis (21) of the needle shaft (12), as seen in FIG. 1.

In one embodiment, the opening (30) of the lumen (28) is substantially free of any cutting surfaces to prevent cutting bodily fibers (not shown) as the needle is inserted. In another embodiment, the edges of the opening (30) of the lumen (28) have been smoothed or otherwise dulled.

In accordance with an embodiment of the present invention, the distal end (42) of the cutting surface (40) may be distal to the opening (30) of the lumen (28) and in one embodiment, the cutting surface (40) will comprise a length less than about 100% of the needle outside diameter, and in another embodiment less than about 50% of the needle outside diameter. (The needle outside diameter is herein defined as the longest linear distance between two points on the outer edge of the distal end (14) of the shaft (12).)

With reference to FIGS. 4, 5, and 5A–F, some of the differences between a standard Tuohy needle (120) and an embodiment of the needle (10) in accordance with this invention include the following. The needle (10) of this invention has a cutting surface (40) at the distal end (14) of the needle (10). In one embodiment the cutting surface (40) is substantially linear and substantially straight, and in another embodiment the cutting surface (40) is substantially linear and curved. The proximal end (43) of the cutting surface may begin at the outer edge (41) of the bottom of the needle shaft (12). In one embodiment, the distal end (42) of the cutting surface may end at the most distal point of the distal end (14) of the shaft (12). In another embodiment, the distal end (42) of the cutting surface may end short of the most distal point of the distal end (14) of the shaft (12); in that embodiment, the distal end (14) of the shaft (12) may be rounded. In one embodiment, the cutting surface (40) comprises a line from a point on the outer edge (41) of the bottom of the needle shaft (12) to the most distal point of the distal end (14) (front of the shaft (12)). In another embodiment, the cutting surface (40) comprises a curve from a point on the outer edge (41) of the bottom of the needle shaft (12) to the most distal point of the distal end (14) (front of the shaft (12)).

In one embodiment, the radial length of the cutting surface (40) is from about 25% to about 90% of the needle outside diameter. In another embodiment, the radial length of the cutting surface (40) is from about 35% to about 70% of the needle outside diameter. In another embodiment, the radial length of the cutting surface (40) is from about 40% to about 60% of the needle outside diameter.

In one embodiment, the axial length of the cutting surface (40) is from about 25% to about 90% of the needle outside diameter. In another embodiment, the axial length of the cutting surface (40) is from about 35% to about 70% of the needle outside diameter. In another embodiment, the axial length of the cutting surface (40) is from about 40% to about 60% of the needle outside diameter.

In one embodiment, the cutting surface (40) is substantially parallel to the shaft (12) of the needle (10). In another embodiment, the cutting surface (40) is within about forty-five degrees of parallel to the shaft (12) of the needle (10) (i.e., plus or minus about forty-five degrees from parallel). In another embodiment, the cutting surface (40) is within about thirty degrees of parallel to the shaft (12) of the needle (10) (i.e., plus or minus about thirty degrees from parallel). In a last embodiment, the cutting surface (40) is within about fifteen degrees of parallel to the shaft (12) of the needle (10) (i.e., plus or minus about fifteen degrees from parallel).

In one embodiment, the shape of the cutting surface (40) approximates the prow of a ship that is from about 0 to about 60 degrees away from parallel with the longitudinal axis of the shaft (12). The proximal end (43) of the cutting surface may begin at the outer edge (41) of the bottom of the needle shaft (12). The distal end (42) of the cutting surface may end at the most distal point of the distal end (14) of the shaft (12).

In another embodiment, needle (10) of this invention has a beveled surface (39) at the distal end (14) of the needle (10). In one embodiment, the beveled surface (39) may be located between the most distal point of the distal end (14) (front of the shaft (12)) and the most distal point of the opening (30) of the lumen (28). In another embodiment, the beveled surface (39) may be located between the distal end of the cutting surface (42) on the bottom of the shaft (12), rounded over the most distal point of the distal end (14) (front of the shaft (12)), and then end at the most distal point of the opening (30) of the lumen (28); in this embodiment, the most distal point of the distal end (14) (front of the shaft (12)) is rounded, and the distal end of the cutting surface (42) is on the bottom of the shaft (12).

In one embodiment, the beveled surface (39) may have a radial length less than about 50% of the needle outside diameter. In another embodiment, the beveled surface (39) may have a radial length less than about 35% of the needle outside diameter. In another embodiment, the beveled surface (39) may have a radial length less than about 25% of the needle outside diameter.

The needle (10) may have a wide range of sharpnesses due to the configuration of the cutting surface (40) in relation to the other components of the needle (10). In one embodiment, the sharpness of the cutting surface (40), as measured by the grams of force required for the needle tip to puncture a sheet of two mil thick polyethylene, is from about 85 grams of force to about 100 grams of force. In another embodiment, the sharpness of the cutting surface, as measured by the grams of force required for the needle tip to puncture a sheet of two mil thick polyethylene, is from about 100 to about 125 grams of force.

Figure 5:
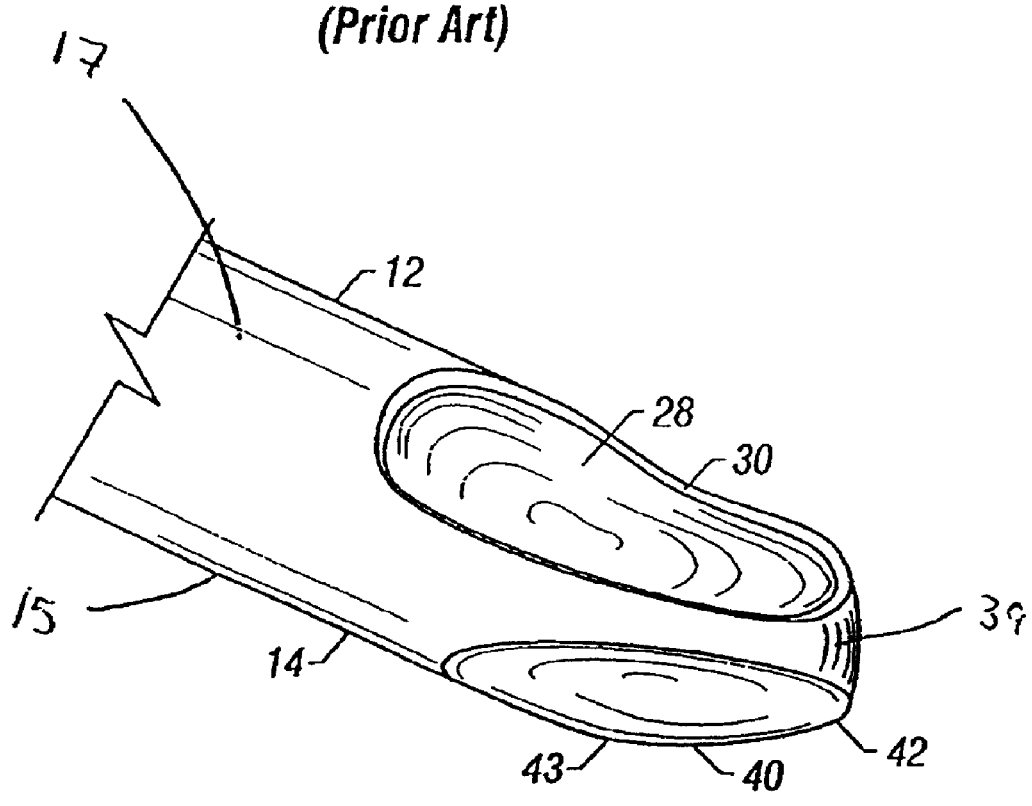
FIG. 5 is a fragmented view similar to FIG. 4 of a needle in accordance with an embodiment of the invention showing the cutting surface and beveled area from the tip of the cutting surface to the lumen.
Figure 5A:
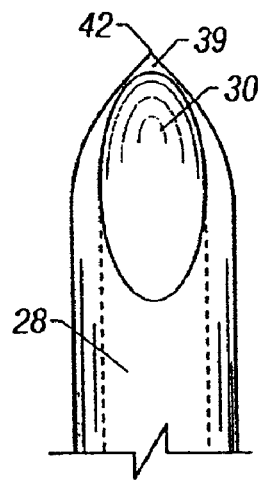
FIG. 5A is an enlarged, fragmentary top elevational view of the tip of the needle of FIG. 5 in accordance with an embodiment of the invention showing the lumen and tip of the cutting surface.
Figure 5B:
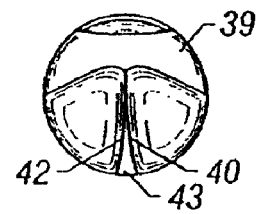
FIG. 5B is a front elevational view showing the cutting surface at the tip of the needle of FIG. 5 in accordance with an embodiment of the invention.
Figure 5C:
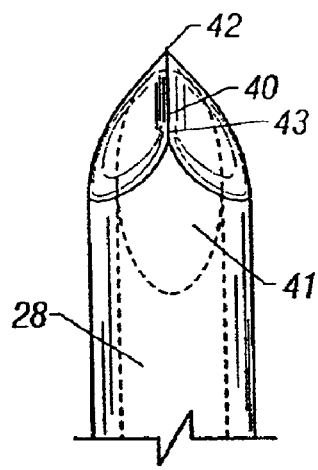
FIG. 5C is a bottom elevational view showing the cutting surface at the tip of the needle of FIG. 5 in accordance with an embodiment of the invention.
Figure 5D:
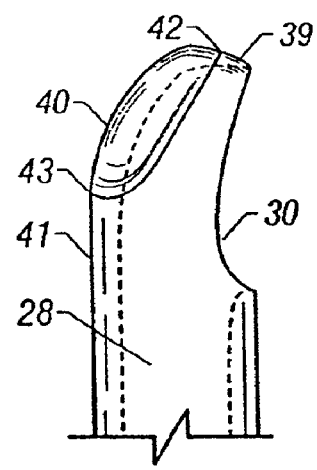
FIG. 5D is a side elevational view showing the cutting surface and the lumen opening at the tip of the needle of FIG. 5 in accordance with an embodiment of the invention.
Figure 5E:
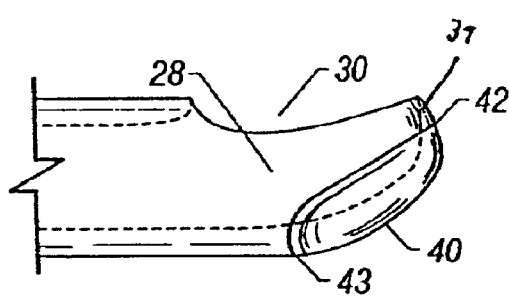
FIG. 5E is a side elevational view showing the cutting surface and a lumen opening at the tip of the needle of FIG. 5 in accordance with an embodiment of the invention.

For clarification, FIG. 5A is a view of the top of the needle (10). The lumen opening (30) is on the top of the needle (10). FIG. 5C is a view of the bottom of the needle (10). The cutting surface (40) extends from its proximal end (43) on the bottom of the needle to its distal end (42) at the front of the needle. FIG. 5B is a view of the front of the needle (10). The front of the needle is its most distal point. The distal end (42) of the cutting surface (40) terminates at the front of the needle. The beveled surface (39) also may be located at the front of the needle (10).

Figure 5F:
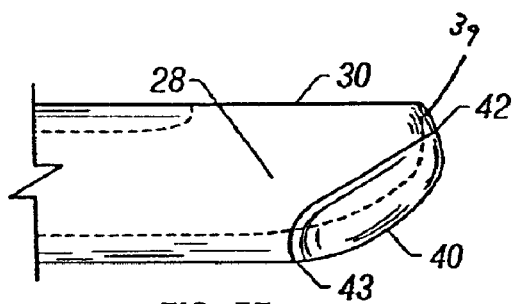
FIG. 5F is a side elevational view showing the cutting surface and a different lumen opening at the tip of a needle in accordance with an embodiment of the invention.

FIG. 5F is a side view of another embodiment of the needle (10). The lumen opening (30) is on the top of the needle (10). The cutting surface (40) extends from its proximal end (43) on the bottom of the needle to its distal end (42) at the front of the needle. The distal end (42) of the cutting surface (40) terminates at the front of the needle. The beveled surface (39) also may be located at the front of the needle (10). The opening (30) of the lumen (28) in this embodiment is located substantially even with or substantially aligned with the outside edge of the distal end (14 in FIG. 1) of the shaft (12 in FIG. 1).

In one embodiment, the needle (10) may be used for a spinal and/or dorsal column stimulation method to implant electrodes. In this method, the electrodes may act to override the nearby nerve responses. In one embodiment, electrodes are unipolar, quadripolar, or octipolar. In another embodiment, the electrodes may be flat electrodes and may be used for dorsal column stimulation.

In another embodiment, the needle (10) may be used for a spinal stimulation method and/or a spinal stimulation trial. Before using the method, the patient may first undergo a screening trial of spinal cord stimulation to determine if the patient is a suitable candidate for this procedure. The screening trial comprises percutaneous placement through the needle (10) of a temporary trial lead into the epidural space overlying the dura and spinal cord. The screening trial also may include the implantation of multiple leads with multiple electrodes. Leads may be placed along the spinal cord axis (parallel to the spinal cord), oblique to the spinal cord axis, or transverse to the spinal cord axis according to methods known in the art of pain management.

In the screening trial, the patient is first taken into the operating room and placed prone on the operating room table. Using fluoroscopic guidance, the spinal levels are identified. The patient is prepped and draped in sterile fashion. The needle (10) is inserted percutaneously into the epidural space using fluoroscopic guidance as well as the loss of resistance technique or other methods. The spinal cord stimulator lead is passed under fluoroscopic guidance into the epidural space overlying the spinal cord until the desired position is achieved.

Figure 2B:
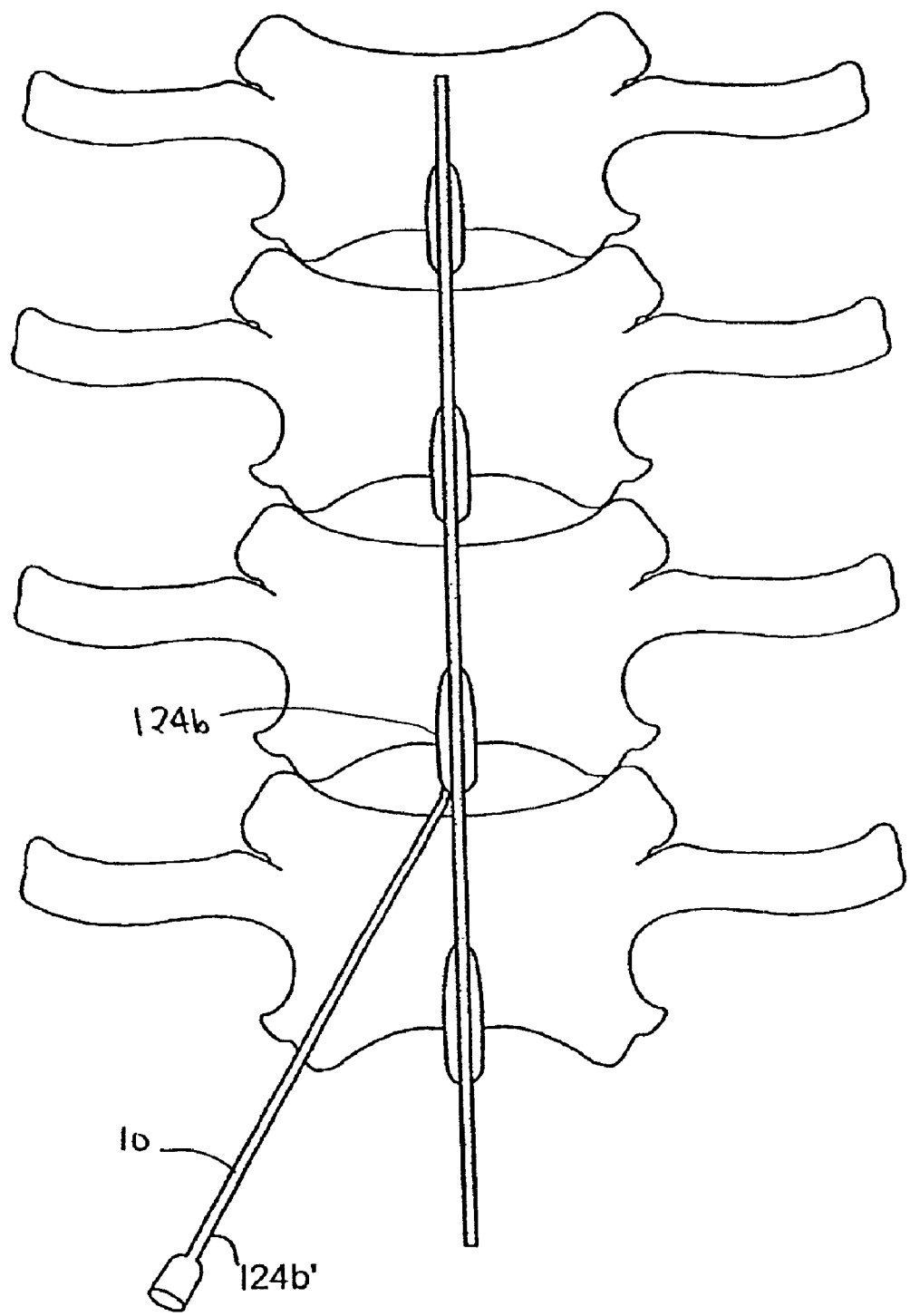

FIG. 2a illustrates needle (10) inserted between spinous processes (125) and passing through ligamentum flavum (126) into the epidural space (127). The distal position of the lead in the cord is identified as (128). The distal lead electrodes overlie the dura (129) and the spinal cord (130). The needle passes through skin (131). FIG. 2a illustrates the lead placement in the side or sagittal view. The anterior posterior view in FIG. 2b illustrates the needle (10) placed at the midline (124b) or in paramedian fashion (124b').

Figure 3B:
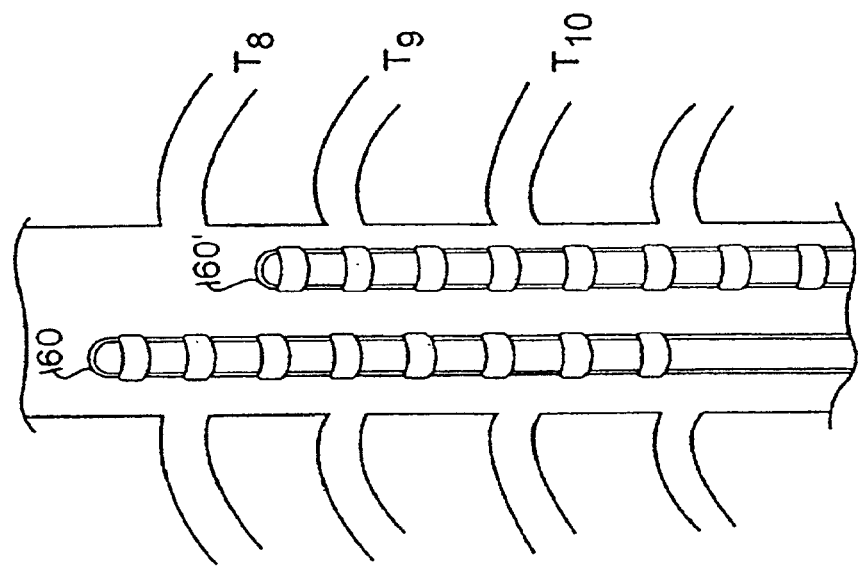
FIG. 3a illustrates a lead placed at the midline of the spinal cord and FIG. 3b illustrates two eight-electrode leads placed in the spinal cord.
Figure 3A:
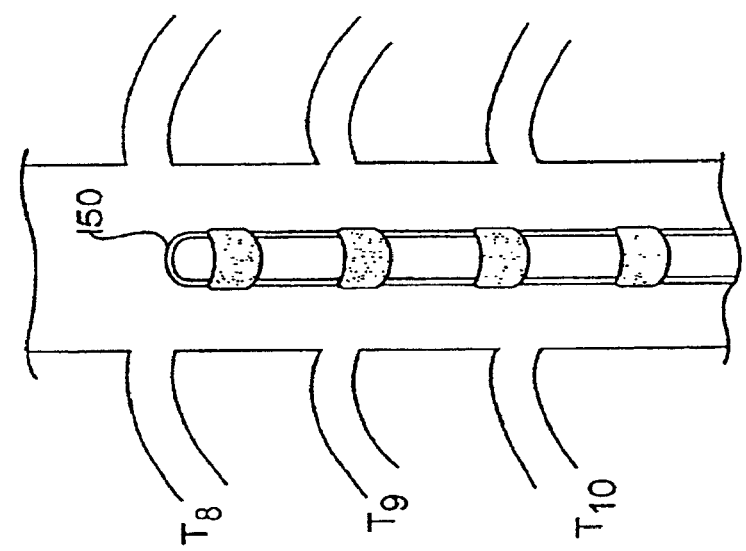
Figure 4:
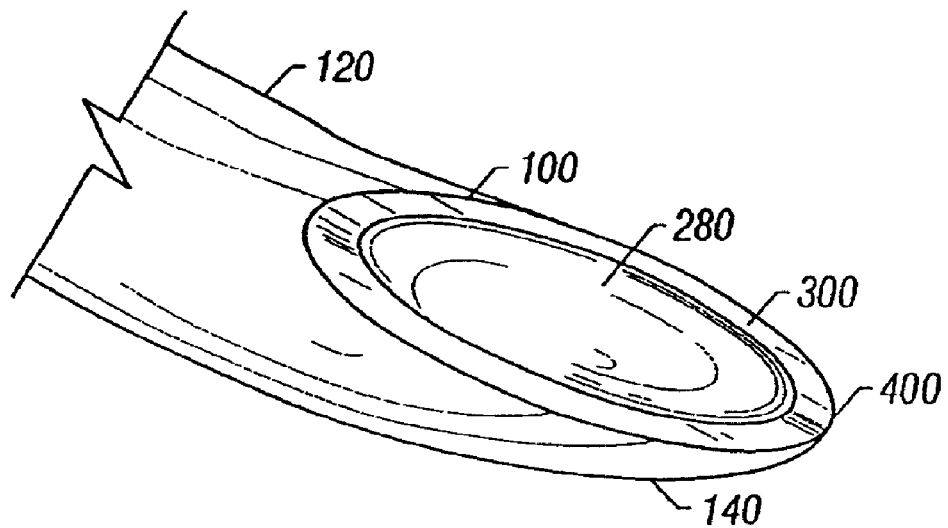
FIG. 4 is a fragmented view illustrating the distal end of a prior art needle.

FIG. 3a illustrates a lead (150) placed at the midline of the spinal cord with the tip at the level of the eighth thoracic vertebral level T8. In FIG. 3b, two eight-electrode leads (160) and (160') are both placed in the spinal cord with lead (160) past the eighth thoracic vertebral level T8 and (160') past the ninth thoracic vertebral level T9. This configuration could also be achieved with 2 four electrode leads or a combination. Leads (160) and (160') may be connected to the same or separate power sources and receive identical or individual programs from the same or different power sources. The two eight-electrode leads (160) and (160') placed in the spinal cord represent an example of a multi-electrode array system.

After placement in the spinal cord, the trial lead or leads are connected to an external power source signal generator via a lead extension connector (not shown) which may be disposable. Variations in amplitude are administered from about 0 to about 15 volts, variations in pulse width from above 0 to about 450 microseconds, variations in pulse shape, variations in rate from about 0 to about 150 cycles per second (Hz), and variations in electrode polarity (i.e., positive/negative polarity in the first, second, third, fourth, fifth, sixth, seventh, etc., conducting electrodes). The stimulation trial begins with basic settings in polarity with the second most distal lead negative and the third most distal lead positive with a rate of 80 and a pulse width of 270. The amplitude is slowly increased from 0 volts until stimulation is detected by the patient. Amplitude requirements are highly variable and depend on both the position of the lead or leads and the contact quality.

Stimulation may be detected when the patient experiences tingling in areas of skin in the back and lower extremities in the case of a thoracic or lumbar spinal cord stimulation, in the areas of skin in the abdomen and chest wall with upper thoracic stimulation or in the areas of skin in the upper extremity and upper chest wall in the case of cervical spinal stimulation. To ensure the lead is placed along the dorsum of the spinal cord (and thus stimulating the dorsal horn), the sensory feeling of tingling is preferable over the motor feeling of pulling or muscle twitching. Dorsal placement also may be verified fluoroscopically. The lead may be superficially fastened to the skin (e.g., with a single suture and sterile barrier dressing) for easy removal at the end of the trial. Alternatively, the lead may be partially internalized. The latter procedure involves extending the needle puncture site into a small incision, anchoring the lead to the spinous ligaments with suture and tunnelling a temporary lead extension connector to a distal exit site. The partial internalization procedure preserves the lead for permanent use (the temporary connector is discarded) but requires a more extensive removal procedure in the event of a failed trial.

The screening trial may extend from about 3 to about 10 days or more with frequent evaluation of the patient's response. The evaluations may comprise subjective reports from the patient. The evaluations also may include objective evidence. At the end of the screening trial, a decision on whether on not to permanently implant the lead will be made based on criteria for success. These criteria will include patient symptoms experienced before and during the trial. If the screening trial is considered successful, then the patient may proceed with permanent implantation of the spinal cord stimulator system. Permanent implantation may include removal of the trial screening lead (or leads) and subsequent re-implantation of a new spinal cord stimulator lead (or leads), power source and internal lead extension connector. Alternatively, the permanent implantation procedure may include internalization of the trial screening lead (or leads) if this lead (or leads) was anchored and tunneled (i.e., partially internalized to remain sterile) during the trial.

Permanent implantation of the spinal cord stimulator lead or leads after a successful screening trial comprises the placement of a permanent spinal cord stimulator lead or leads (similar or identical to the trial lead if percutaneously placed, paddle lead if placed through laminotomy). Placement of the permanent lead or leads is performed by the same method used for implantation of the trial screening lead (if percutaneous not laminotomy). In the permanent implantation procedure, the patient may be taken to the operating room and placed in the prone position with fluoroscopic guidance as described for the screening trial procedure. The spinal level selected is similar but not necessarily identical to the trial screening level in the sacral, lumbar, thoracic or cervical areas. A spinal cord stimulator lead or leads are placed as described for the screening trial procedure. Once stimulation reproduces the stimulation observed with the trial lead or leads, the percutaneous insertion sites are extended as an incision using a scalpel to include the sterile lead extension connector pocket. Alternatively, laminotomy or laminectomy may be performed with placement of a surgical lead. A distal site is selected for the permanent signal generator or receiver implantation and a tunnel is made from the midline incision (where lead placement occurs) to the distal pocket site for the energy source.

Figure 6:
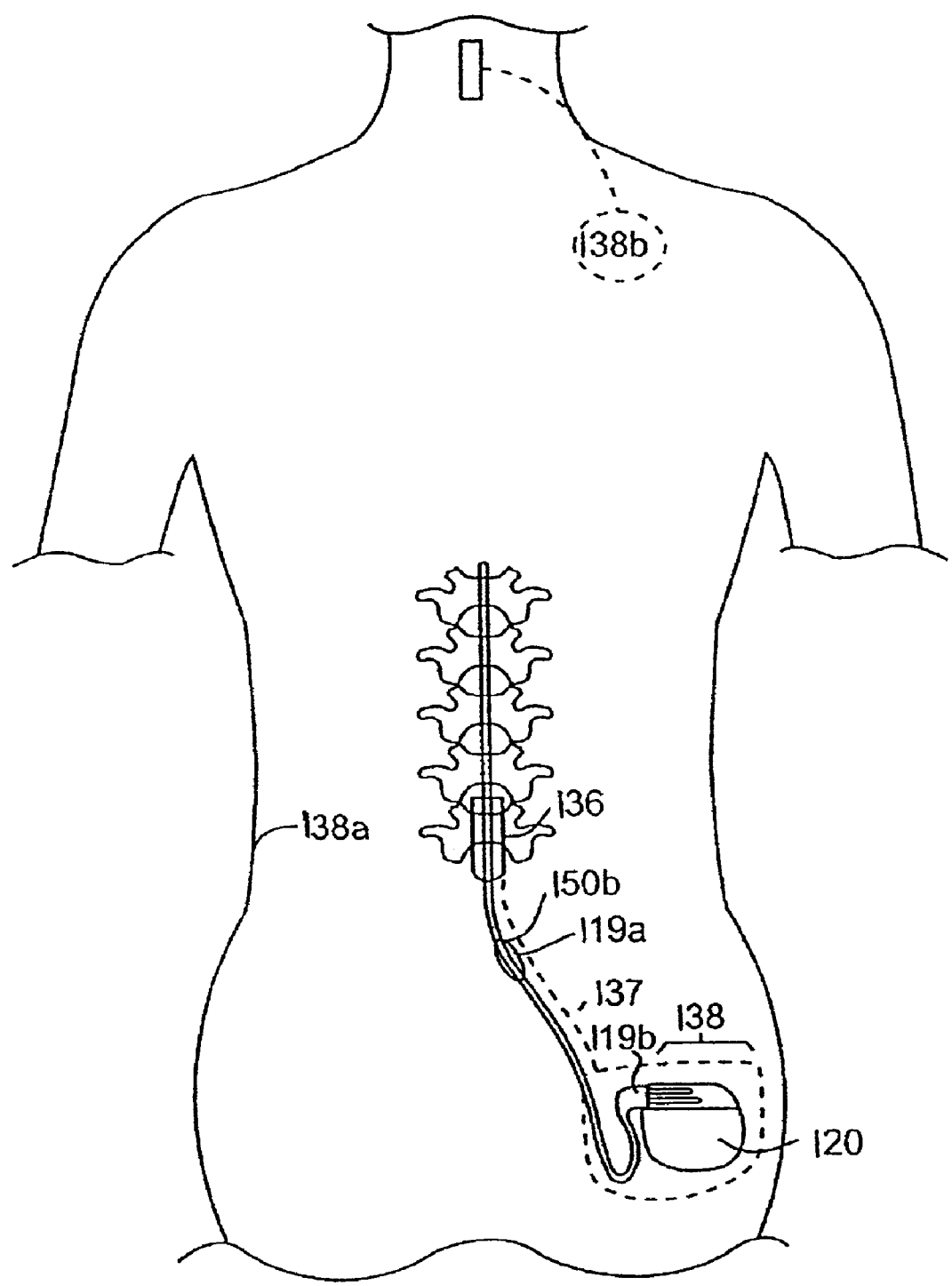
FIG. 6 illustrates an implantation of the spinal cord stimulation system.

As illustrated in FIG. 6, the lead extension connectors may pass through the tunnel to form a connection between the proximal end of the spinal cord stimulator lead and the power source generator or receiver as described previously. The proximal end of spinal cord stimulator permanent lead (150b) extends from a midline incision (136). A tunnel (137) is made from the midline incision (136) to a distal pocket site commonly made in the upper buttocks (138), in the anterior abdomen (138a) or the upper chest (138b) in cervical stimulation. Lead extension connector distal connector site (119a) is connected to the proximal end of the spinal cord stimulator lead (150b) and the proximal end of the lead extension connector (119b) is connected to the internal energy source (or receiver) (120) which lies in the distal pocket.

In a permanent implantation, the implanted lead or leads may remain in place for a time period between about one month to about ten years. Shorter time periods are also possible. For example, the implanted lead or leads may remain in place for a time period between about one year to about five years. The time period of implantation also may extend between about one year to about two years.

The patient may be followed up immediately post-implantation according to standards for routine post-operative care and wound checks (approximately two times per week for the first week). The patient may be seen about twice a week for the first week, about once per week for the next seven weeks and then about once per month through the end of the first year.

Given the variety of available leads, lead systems, power sources and procedural combinations, many approaches are possible and viable for use in treatments. Improvements of the device and method may include the use of multiple lead types, electrode numbers, multi-channel leads placed, paddle leads, multiple generator input of multiple leads for single generator, multiple generators, implanted receivers with external power sources connected to single or multiple leads with various number of electrodes. Settings for these leads may be identical as when inserted into single generator power source or may be independent of each other. There can be transmission from one lead electrode to another electrode on the same lead or there can be transmission from lead electrode or electrodes on a single lead to electrodes on a different lead or to multiple other leads.

Computer programs also may be used to program a complex network for transmission between multiple leads and multiple-lead electrodes for the maximum transmission into and through the spinal cord. This can be performed at multiple levels including low lumbar up to high cervical with most likely positive results being in the mid to low thoracic area. Electrode polarities from distal to most proximal two electrode, four electrode, eight electrode, and even higher electrode numbered systems can vary polarity positive to negative in each of the two, four, eight, and sixteen electrodes with all permutations of positive and negative included. Any electrode on a given lead can transmit and communicate to any electrode on a separate lead in combination with polarity changes and multiple permutations. Besides electrode polarity, placement of single or separate leads in addition to covering all levels of the spinal cord may comprise two or more separate locations within the spinal cord. For example, one lead may be placed low lumbar with another lead placed thoracic with communication between the two leads or independent stimulation between the two leads. Paddle lead systems may be inserted through laminotomies or percutaneously (if feature variations are made), and these may be used independently, with multiple paddle leads or with combinations of percutaneous leads.

As note above, the settings for electrical stimulation include amplitude, rate and pulse width/shape along with polarity of contact electrodes. Additionally, the current art for spinal cord stimulation includes continuous mode stimulation or cycling mode stimulation. Continuous mode stimulates continuously and may be required long-term for optimal results. Cycling mode stimulation automatically provides alternating periods of stimulation of no stimulation of varying durations. The use of cycling mode can significantly increase the battery life in totally implanted systems. In addition to continuous and cycling modes, biphasic stimulation allows electrode polarity to reverse periodically, e.g., with every pulse. Single stimulation, dual stimulation and multiple electrode stimulation arrays are also available. This allows stimulation of single lead of 1, 4, 8 or 16 electrodes (projected greater number of electrode leads to become available). Dual stimulation provides different stimulation programs for separate channels for the generator power source to two sets of electrodes (two four-electrode leads, two eight-electrode leads), or differing stimulation to the two sets of four electrodes or two sets of eight-electrode leads. Pulse width, amplitude and rate may be the same for both channels. Future variations are expected to provide additional versatility in multiple lead systems having even greater numbers of electrodes.

In another embodiment, the needle (10) of this invention may be employed for pain management applications to implant a catheter to deposit medications into the epidural space, on a paravertebral nerve root, or in the neural foramen, or for a catheter to cannulate the neural foramen for any reason.

Figure 7:
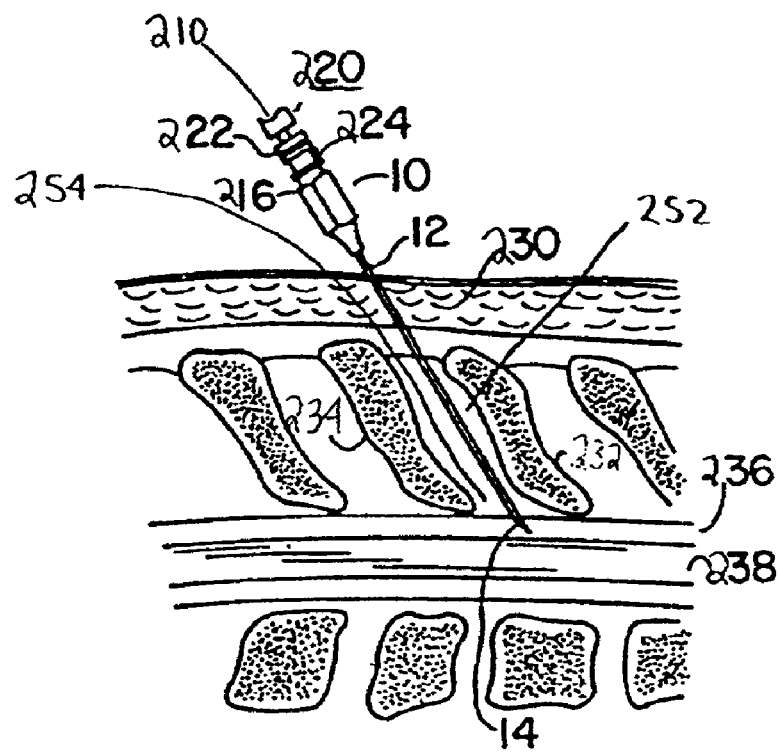
FIG. 7 is a perspective representation in partial cross-section of the percutaneous insertion of the assembled introducer needle and stylet.
Figure 8:
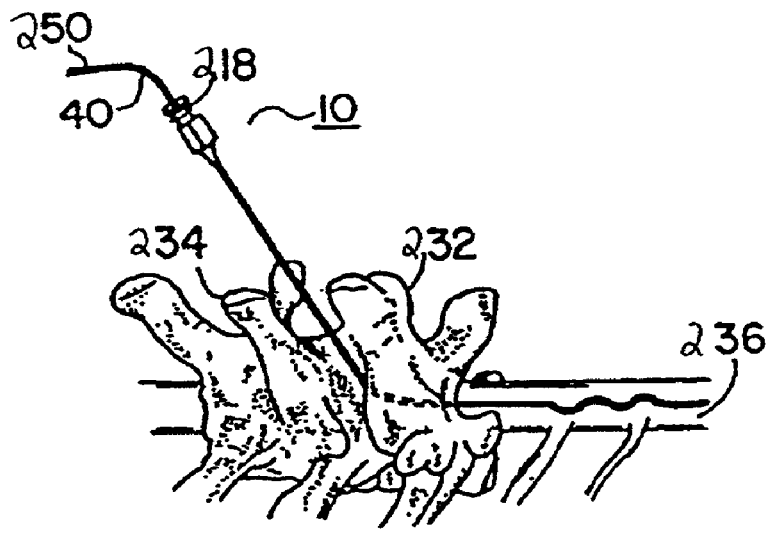
FIG. 8 is a perspective representation of the advancement of a lead and stylet into the epidural space.

In one embodiment, the needle (10) is used for a catheter installation and fixation procedure as illustrated in FIGS. 7 and 8, which depict the operative procedure of introducing one of the catheters into the epidural space (236) adjacent the spinal cord (238). The needle (10), which may be between about 14 and about 18 gauge, and a stylet (210) for stiffening the needle (10), are inserted into the interspinous ligament (252) between adjacent vertebrae (232) and (234) until the distal end (14) of the needle (10) is advanced through the ligamentum flavum (254) and into the epidural space (236). The stylet (210) then may be withdrawn and a wire guide (not shown) may be inserted through the needle into the epidural space under fluoroscopic control to identify a pathway that the catheter (250) may take. The operative procedure may be repeated until an appropriate pathway is identified.

Penetration of the ligamentum flavum (254) may be confirmed by withdrawing the stylet (210) and filling the needle lumen (28) with saline solution, which rapidly drains when penetration is achieved.

Thereafter, the wire guide (not shown) may be removed and a catheter (250) inserted through the catheter adapter (218) into the needle lumen (28), and then into the epidural space (236). Under fluoroscopic control, the catheter (250) is advanced to an appropriate spinal level under manipulation of the needle (10) and the catheter (250) itself. The catheter (250) depicted in FIG. 2 in the epidural space may possess a relaxed curved shape which may be straightened by insertion of a catheter stylet (not shown). Once the catheter (250) has been positioned as desired, the proximal end of the catheter may be coupled to a medication dispenser (not shown).

The needle (10) used in such implants may have a sharpened, curved distal end (14) with a cutting surface (40) to facilitate both the penetration of the subcutaneous fascia (230) as well as the underlying interspinous ligament (252) and ligamentum flavum (254), and a lumen opening (30) to guide the direction of the wire guide (not shown) and implantable catheter (250) at an angle to the axis of the needle (10) as shown in FIGS. 7 and 8. The stylet (210) may be provided with a matching beveled end such that when it is fully inserted into the lumen of the needle (10), the beveled surface may be lined up to the lumen opening (30) to both stiffen the entire assembly and block the opening in the distal end of the needle, thereby easing its introduction. To avoid the inadvertent rotation of the stylet (210) within the lumen of the needle during percutaneous advancement of the assembly, a notch (224) may be provided in the needle hub (216) which receives a complimentary lug (222) on the stylet hub (220). During introduction, as shown for example in FIG. 7, manual force may be applied to the two hubs to maintain the lug within the notch and prevent the inadvertent rotation or backing out of the stylet (210).

In another embodiment, the needle (10) of this invention may be employed to implant a catheter in the epidural space or the neural foramen for mechanical and/or chemical lysis of adhesions. Mechanical lysis of adhesions is known in the art and may involve using force to pierce the catheter through the adhesion. Chemical lysis of adhesions also is known in the art and may involve administering one or more medications to soften the adhesions chemically.

In another embodiment, the needle (10) of this invention may be employed to implant a catheter in the epidural space for continuous delivery of medications. In one embodiment, the catheter may be implanted for about four weeks to about eight weeks. Suitable applications include cancer patients, hospice patients, sports injury rehabilitation, rehabilitation of any kind, stroke patients, and patients with neuropathic pain or sympathetically mediated pain syndromes.

In another embodiment, the needle (10) may be used to implant electrodes, catheters, surgical tools, cameras, lasers, heating and cooling mechanisms, probes, cutting tools, lights, and other types of apparatus that can be passed through the lumen (28) of the needle (10) in order to carry out a variety of procedures.

In one embodiment, the needle (10) may be used in a method of epidural surgery that improves visibility in the epidural space of a patient for more effectively conducting therapeutic surgery in and around the epidural space, such as applying a steroic fluid, performing a diskectomy, or disrupting a fibrotic lesion. A method of epidural surgery according to the present invention involves distending a portion of the epidural space by filling the portion of the epidural space with a fluid; in one embodiment a liquid, such as a saline solution, is supplied from a catheter positioned in the epidural space. As shown in FIGS. 9–19, a portion of an optical scope (360) may be positioned in a distended portion of the epidural space by inserting the optical scope (360) through the catheter (330) to provide a visual image of the epidural space.

The catheter (330) may be one of the numerous types of catheters known to those skilled in the art, or may be a multi-lumen, steerable catheter (330) as illustrated with reference to FIGS. 9–10. The multi-lumen, steerable catheter (330) may have a multiple durometer tube portion (340) extending outwardly from a handle portion (335). The optical scope (360) may be a 0.88 millimeter (mm) fiberscope, known in the art, that may be inserted through a lumen (341) of the steerable catheter (330), and optionally through a fiberoptic sheath (361) as shown in FIG. 9 and have a portion (362) thereof extend into the epidural space. The fiberscope (360) may communicate with an imaging apparatus.

By providing the combination of the steerable catheter (330), the fiberscope (360), and the imaging apparatus (not shown), a physician, or other medical personnel, can control and manipulate the catheter (330) and the imaging source of the imaging apparatus (not shown) while simultaneously using surgical tools, such as cutting instruments or the like, and fluids needed for medical operations to thereby allow the physician to positionally locate, isolate, and view problem areas within the epidural space on a monitor, i.e., a television or other visual display. The imaging apparatus not only enables the physician to observe the visual image of the distended portion of the epidural space, but also provides a means for recording and documenting the problem area using a data recorder, such as a video cassette recorder which may be on a portable stand together with a viewing monitor. Because the steerable catheter (330) may be quite flexible and maneuverable within the epidural space, as shown in FIG. 11, the method provides potentially less radical interspinal surgical operations because problem areas can more effectively be observed and accessed with the optical scope (360) and steerable catheter (330) combination. Because the imaging apparatus may be mounted on a stand having wheels, the physician and other medical personnel can position the apparatus close to the operation site. A control panel and imaging source can be provided for image adjustments, focus, and magnification to assist in viewing the epidural space and the problem area when the portion of the epidural space is distended by the liquid. It will be understood that the distended portion of the epidural space to be viewed may be an amount of the epidural space less than the entire boundaries thereof.

With reference to the block diagrams illustrated in FIGS. 13 and 14, the method of epidural surgery according an embodiment of the present invention includes inserting the needle (10) through the skin of a patient, in one embodiment through a sacrum region or a lumbar region of the patient, and into the epidural space to provide an opening from the skin into the epidural space of the patient.

Figure 19:
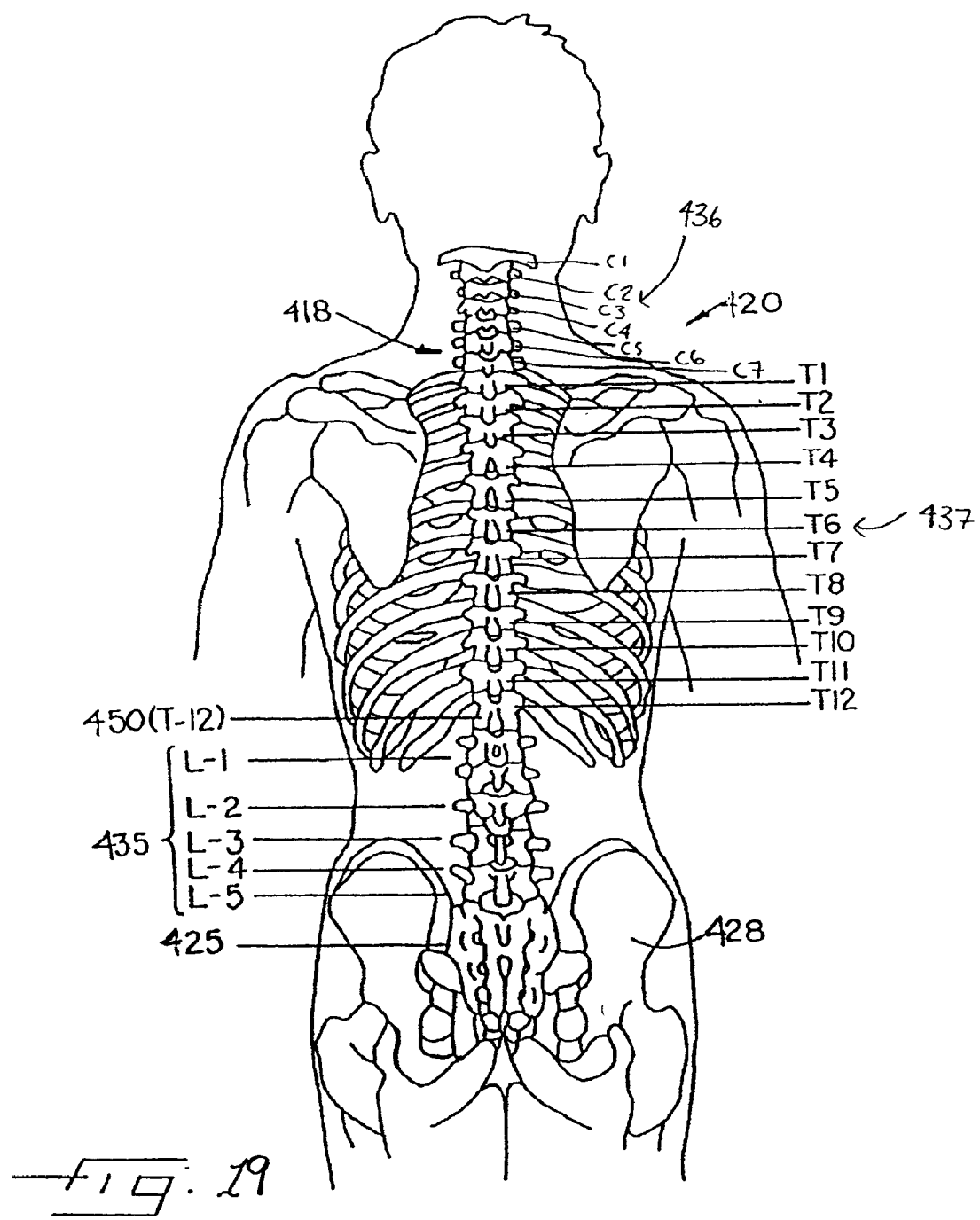
FIG. 19 is a fragmentary skeletal view of a human body illustrating spinal column regions thereof.

As illustrated in FIG. 19, the sacrum region (425) is at a lower end of the spinal column (418) below L-5 and adjacent the pelvic region (428). The sacrum (425) is a triangular-shaped bone formed generally by five fused vertebrae, i.e., sacral vertebrae, that are wedged dorsally between the two hip bones of the pelvic region (428) in this region of the human anatomy. It also will be understood by those skilled in the art that the invention may be used for various animals for veterinary epidural procedures. The lumbar region (435) extends from L-1 to L-5 between the sacrum region (425) at a lower end and the thorax region (437)(T-1 to T-12) at an upper end. The thorax region (437) extends from T-12 (450) to T-1 at the base of the cervical region (436). The cervical region (436) extends from C1 to C7. In one embodiment, the invention may be used to insert a needle into the lumbar region (435) in order to advance a catheter into the thorax region (437). In another embodiment, the invention may be used to insert a needle into the thorax region (437) in order to advance a catheter into the cervical region (436).

Figure 17:
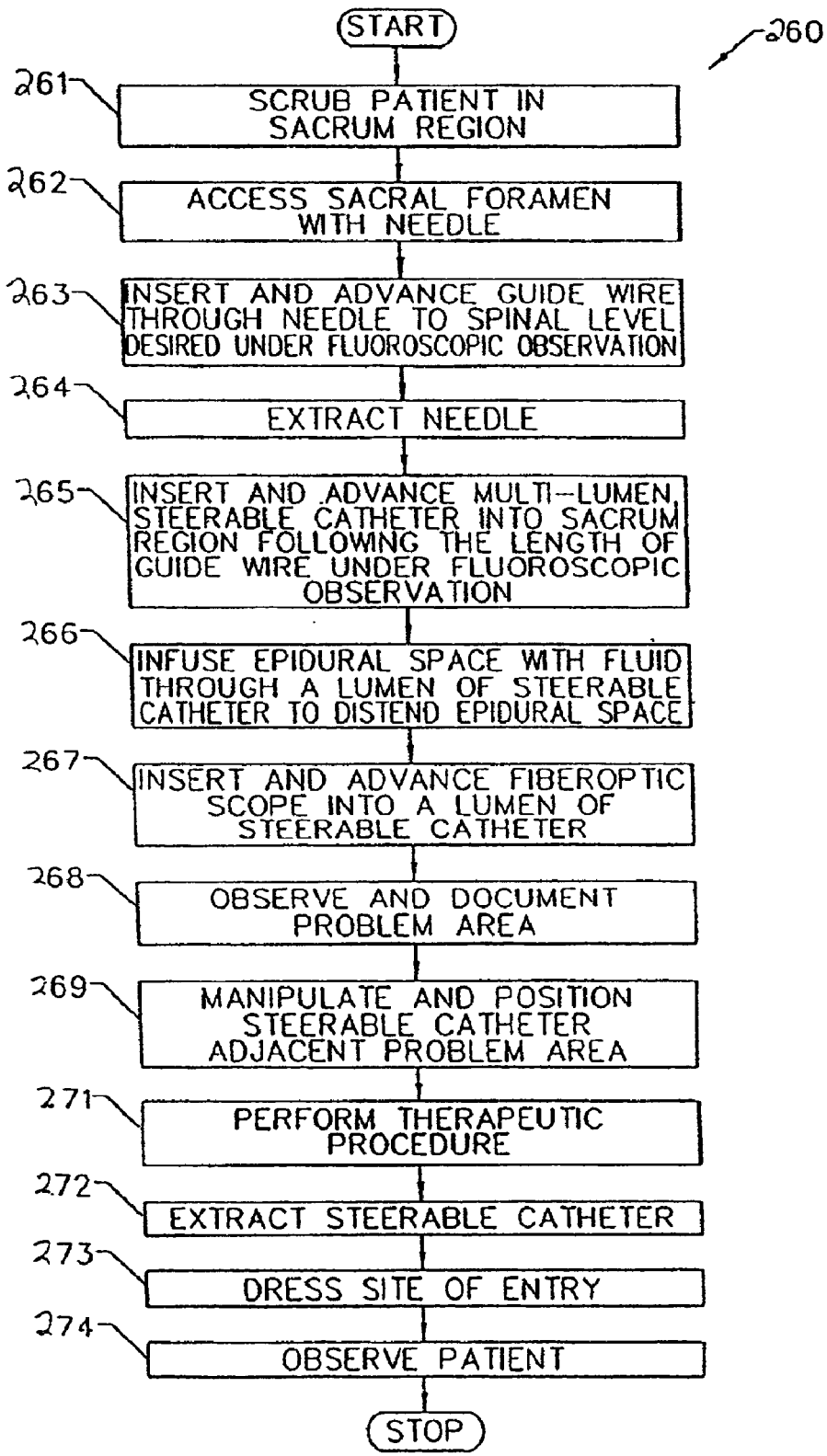
FIG. 17 is a block diagram of a method of epidural surgery according to an embodiment of the present invention.
Figure 18:
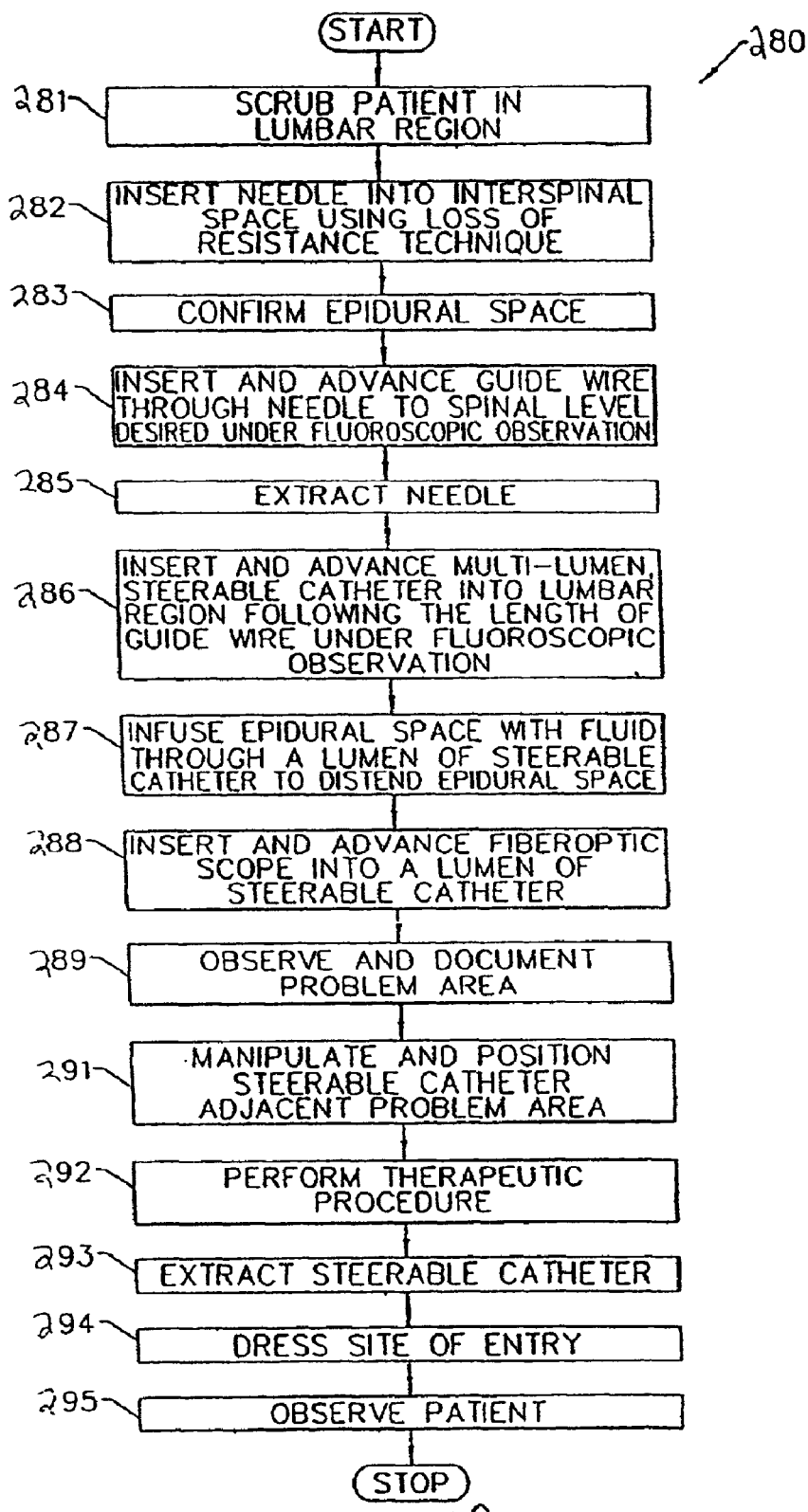
FIG. 18 is a block diagram of a method of epidural surgery according to an embodiment of the present invention.

As illustrated in FIG. 17, according to one embodiment of a method of epidural surgery (260) according to the present invention, the patient is scrubbed in the sacrum region (425), preferably in an area around the sacral canal and up to the level of T-8 (FIG. 19), with wide prep iodine, as shown by block (261). The patient is draped, and the physician is scrubbed and dressed in a sterile gown. The entry site is prepared and a one percent (1%) Xylocaine solution may be injected to create a skin wheel. The patient then may be treated with Versed, which is titrated to the patient's needs. The patient also may be monitored with pulse oximetry, EKG, and/or a blood pressure monitor.

After the patient is scrubbed and prepared, the needle (10) is used to access the sacral foramen, as shown by block (262). The ligamentum-flavum is pierced and the needle tip is inserted in the sacral hiatus. Under fluoroscopic guidance, as shown by block (263), a guide wire, in one embodiment, a 0.035-inch straight tip floppy guide wire, is inserted and advanced through the needle (10) and into the epidural space. The guide wire may be radiopaque and formed of stainless steel with a Teflon coating. The physician then may observe fluoroscopically the position of the guide wire in the epidural space and advance the guide wire to a spinal level where a suspected problem area within the epidural space may have originated. As shown by block (264), the needle is extracted from the epidural space and may be discarded.

The catheter (330), in one embodiment a multi-lumen, steerable catheter, is inserted over the guide wire and into the opening to the epidural space, as shown by block (265). The guide wire functions as a guidance device as the catheter (330) is advanced into the sacral hiatus. Because the catheter (330) may be a steerable catheter, the handle (335) and flexible distal end (345) ease the advancement and positioning of the catheter (330) within and around the epidural space. Fluid is supplied, and optionally continuously supplied, to a lumen (342) of the steerable catheter (330) to distend a portion of the epidural space. The fluid may be a liquid such as a normal saline solution. A normal saline bag can be accessed with an I.V. set and coupled to a three-way valve for fluid regulation. A 20 cubic centimeter (cc) syringe may be coupled to a second port of the three-way stop-cock. An access port to a lumen (342) of the catheter (330) also may be coupled to a third port of the valve. The fluid also may enter through tube portion (338) at a proximal end (337) at the handle portion (335) of the catheter (330) (as shown in FIG. 10). A 20 cc syringe may be used first to extract all the air bubbles from the I.V. set and then to fill the I.V. set with a normal-saline, liquid solution for distention of the epidural space. Twenty cc's of saline can be infused into the epidural space 20, as shown by block (266). The 20 cc's are sufficient to increase the pressure in a portion of the epidural space and create a cavity in which the nerve root or other structures can be observed. The position of the steerable-catheter (330) within the epidural space also may be fluoroscopically observed. The catheter (330), like the guide wire, also may be radiopaque. Under such circumstances, the physician can advance the steerable catheter (330) under the fluoroscopical observation to the suspected problem area.

As shown by block (267), an optical scope (360), in one embodiment a fiber optic scope or fiberscope, is inserted within another lumen (341) of the multi-lumen, steerable catheter (330). The fiberscope (360) can enter an access port in the handle portion (335), as shown in FIG. 10, or enter at a proximal end (337) of the handle portion (335). It also will be understood that the fiberscope (360) can be inserted prior to the advancement of the catheter (330) in the epidural space. A portion of the optical scope (360) is advanced within the lumen (341) of the steerable catheter (330) and into the distended portion of the epidural space. The optical scope (360) may not be radiopaque and may be extended into the epidural space up to one centimeter (cm). With the fluid distending a portion of the epidural space, the optical scope (360) also can be positioned within the distal tip (345) of catheter (330) and still view the distended portion of the epidural space. The optical scope (360) illuminates the distended portion of the epidural space to visualize and display the epidural space and a problem area therein with the imaging apparatus, as shown by block (268). The catheter (330) can be manipulated to place the distal end (345) into an optimal position to avoid adhesions or naturally occurring fat globules that could hinder the flow of drugs, such as a steroic fluid, or that could hinder positioning of instruments or devices used in surgical procedures. As shown by block (269), the catheter (330) is manipulated until the problem area, such as an inflammation, is recognized by its redness, increased vascularity, or other symptoms. The problem area then is observed and documented. As shown by block (271), a treatment is performed to the problem area within the epidural space, such as the application of a steroid or other medication to a nerve area, disrupting a fibrotic lesion, performing a diskectomy, or other types of procedures. These therapeutic treatments may include positioning a distal end (345) of the steerable catheter (330) adjacent the problem area within the epidural space and treating the problem area within the epidural space through a lumen (341) or (342) of the steerable catheter (330).

After performing the treatment, the catheter (330) may be slowly extracted and a dressing placed at the site of entry, as shown by blocks (272), (273). The patient is observed, preferably for about two hours, then may be discharged, as shown by block (274). The patient's chart is completed and a one week follow-up appointment may be made.

As illustrated in FIG. 14, according to another embodiment (280) of a method of epidural surgery of the present invention, a lumbar region (435) of the patient is scrubbed and prepped, preferably in and around the L3–L4 area (FIG. 19), as shown by block (281). In this embodiment, in contrast to the embodiment as illustrated in FIG. 17, the patient may be in a sitting position to spread the L1–L5 vertebrae to make access easier. It also will be understood that other sites of entry along the spinal column (418), besides the sacrum or caudal region (425) and lumbar region (435) of the patient, may be performed according to the present invention.

As shown by block (282), the needle (10) is inserted into the interspinal space, such as between L3 and L4, using the loss of resistance technique known in the art. The epidural space is confirmed and a guide wire, in one embodiment a 0.035-inch straight floppy top guide wire, may be inserted and advanced through the needle (10) to the spinal level where the suspected problem area may be located in and around the epidural space, as shown by blocks (285), (286). The needle (10) then may be extracted (block 285) and discarded.

As shown by block (287), the catheter (330) may be inserted and advanced over the guide wire to the suspected problem area. The epidural space is infused with a fluid, as previously described, and distended (block 287). A portion of the optical scope (360) is inserted and advanced through a lumen (341) of the catheter (330) and into the distended portion of the epidural space, as shown by block (288). The problem area is observed and documented, and the catheter (330) is manipulated and positioned adjacent the problem area for more effectively performing a therapeutic procedure, such as previously described (blocks 289, 291). A therapeutic procedure is performed, also as previously described, as shown by block (292). The catheter (330) may be slowly extracted, and the entry site dressed, and the patient observed (blocks 193–195). A follow-up visit may be scheduled and the patient discharged.

The method of the present invention thereby provides visualization of the epidural space and treatment of problems areas therein. The method allows the physician to observe and document the problem area and then determine the most effective treatment for the patient. Since the steerable catheter (330) may be quite flexible and maneuverable within the epidural space, the method also may provide less radical interspinal surgical operations because problem areas can be observed and accessed with the optical scope and steerable catheter combination.

Figure 20:
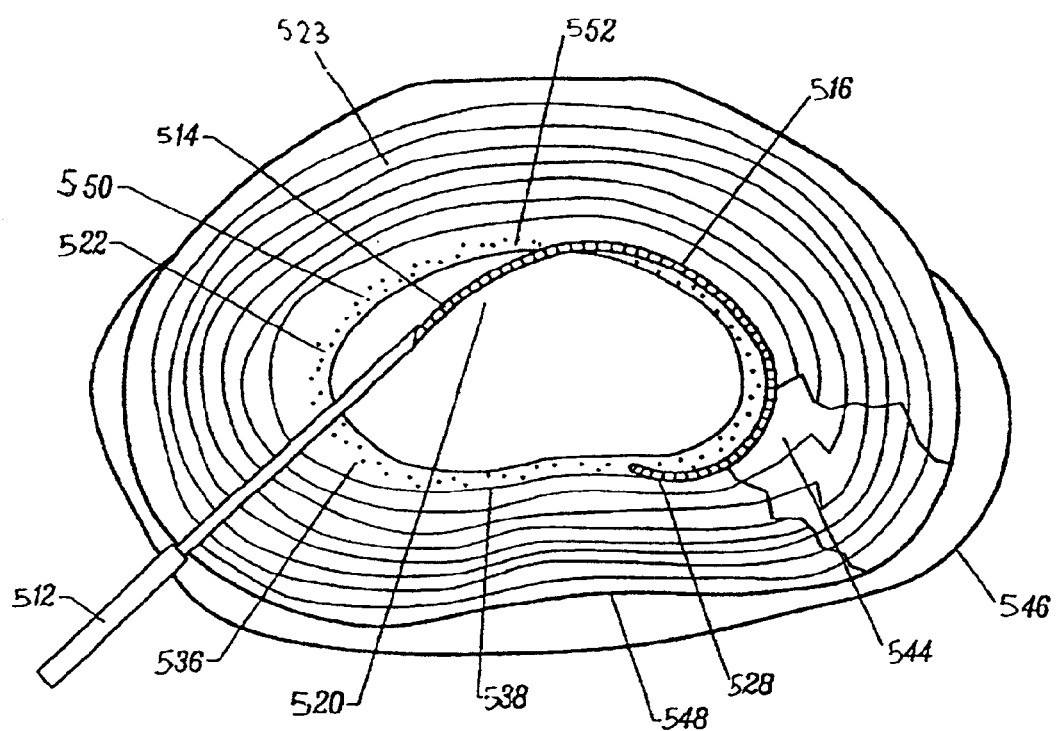
FIG. 20 is a cross-sectional view of an intervertebral disc with a portion of an intervertebral apparatus inserted in the intervertebral disc according to an embodiment of the present invention.

In another embodiment, the needle (10) may be used in a method of intradiscal therapy. Suitable intradiscal therapies include administration of medications, laser therapy, Intra-Discal Electro-Thermy (IDET), heated wire therapy, nucleoplasty, etc. These therapies may be effective in treating bulging and/or pinched disks, sciatic pain, and pinched nerves. IDET may be used as a heat therapy to shrink a bulging disk. Nucleoplasty may be used as a heat therapy to shrink a portion of a disk that is impinging on a nerve. One example of such a therapy is illustrated in FIG. 20. FIG. 20 illustrates the anatomy of an intervertebral disc and shows an apparatus of the invention inserted into a disc. Structures of the disc are identified and described by these anatomical designations: the posterior lateral inner annulus (536), posterior medial inner annulus (538), annulus fibrosus (522)/ nucleus pulposus (520) interface, the annulus/dural interface (546), annulus/posterior longitudinal ligament interface (548), anterior lateral inner annulus (550), and the anterior medial inner annulus (552).

Referring again to FIG. 20, the mechanical characteristics of intradiscal section (516) of catheter (514) may be selected to have (i) sufficient column strength along the longitudinal axis of the catheter to avoid collapse of the catheter and (ii) different flexural strengths along the two axes orthogonal to the longitudinal axis to allow controlled bending of the catheter. These parameters can make the catheter conformable and guidable along inner wall (522) of an annulus fibrosus (523) to reach selected location(s), such as the posterior medial annulus (538).

The necessary design features can be selected (in an interrelated fashion) by first providing the intradiscal section of the catheter with sufficient column strength to be advanceable through normal human nucleus pulposus and around the inner wall of the annulus fibrosus without collapse. Here "collapse" refers to bending sufficient to inhibit further advancement at the tip. Advancement of the tip is restricted by (i) sliding through the normal gelatinous nucleus pulposus, (ii) contacting denser clumps of nucleus pulposus, and (iii) curving and advancing along the inner wall of the annulus. Column strength can be increased in many ways known in the art, including but not limited to selecting materials (e.g., metal alloy or plastic) with a high resistance to bending from which to form the catheter, forming the structure of the catheter with elements that add stiffening (such as bracing), and increasing the thickness of the structural materials. Column strength can be decreased to favor bending by selecting the opposite characteristics (e.g., soft alloys, hinging, and thin structural elements).

When the catheter collapses, the physician may feel an abrupt decrease in resistance. At that time, the catheter forms one or more loops or kinks between the tip of the introducer and the distal tip of the catheter.

Returning now to FIG. 20, intradiscal section (516) may be guidable and can reach the posterior, the posterior lateral, and the posterior medial regions of the posterior wall of the annulus fibrosus, as well as other selected section(s) on or adjacent to inner wall (522). In order to move the functional section of the catheter into a desired nucleus location, intradiscal section (516) is first positioned in the nucleus pulposus (520) by means of the needle (10).

The needle (10) may pierce the annulus fibrosus (523) and be advanced through the wall of the annulus fibrosus into the nucleus pulposus. In such embodiments, needle (10) is extended a desired distance into the nucleus pulposus (520). Catheter (514) is advanced through a distal end of needle (10) into the nucleus pulposus (520). Advancement of the catheter (514), combined with increased resistance to advancement at the annulus fibrosus, causes the tip of the intradiscal section to bend relative to the longitudinal axis of needle (10) when the intradiscal section contacts the inner wall of the annulus fibrosus (523). Catheter (514) is navigated along inner wall (522) of the annulus fibrosus (523) to selected site(s) of inner wall (522) or within the nucleus pulposus (520). For example, intradiscal section (516) can be positioned in or adjacent to a fissure or tear 44 of the annulus fibrosus (523).

The distal portion (528) of intradiscal section (516) is designed to be incapable of piercing the annulus fibrosus (523). The inability of distal portion (528) to pierce the annulus fibrosus (523) can be the result of either the shape of the tip (529) or the flexibility of the distal portion (528), or both. The tip (529) is considered sufficiently blunt when it does not penetrate the annulus fibrosus but instead is deflected back into the nucleus pulposus or to the side around the inner wall of the annulus when the tip (529) is advanced. The tip can be made with a freely rotating ball. This embodiment provides not only a blunt surface but also a rolling contact to facilitate navigation.

Many percutaneous and endoscopic instruments designed for other purposes can be adapted for use in this invention. This permits other functions at the desired location after the catheter is advanced to that position. For example, cutting edges and sharp points can be present in the distal portion (528) if they can be masked temporarily by a covering element. However, such devices must be sufficiently flexible and thin to meet the design characteristics described in this specification.

In another embodiment, the needle (10) pierces the skin and reaches the exterior of the annulus fibrosus (523). A rigid and sharp trocar is advanced through needle (10), to pierce the annulus fibrosus (523) and enter the disc. The trocar is removed, and catheter (514) is advanced through a distal end of needle (10), following the path created by the trocar in the annulus fibrosus (523) beyond the end of the introducer. In such cases, the needle is outside the annulus fibrosus (523) and only the catheter with its guidable distal portion (516) is present inside the disc. The physician can manipulate the proximal portion (not shown) of the catheter to move the distal portion of the catheter to a selected location for treating a fissure of the annulus fibrosus (523).

Catheter (514) is not always pre-bent, but optionally can include a biased distal portion (528) if desired. "Pre-bent" or "biased" means that a portion of the catheter (or other structural element under discussion) is made of a spring-like material that is bent in the absence of external stress but which, under selected stress conditions (for example, while the catheter is inside the needle), is linear. Such a biased distal portion can be manufactured from either spring metal or superelastic memory material (such as a nickel-titanium alloy). The needle (at least in the case of a spring-like material for forming the catheter) is sufficiently strong to resist the bending action of the bent tip and maintain the biased distal portion in alignment as it passes through the needle. Compared to unbiased catheters, a catheter with a biased distal portion (528) encourages advancement of intradiscal section (516) substantially in the direction of the bend relative to other lateral directions. Biasing the catheter tip also further decreases likelihood that the tip (529) will be forced through the annulus fibrosus under the pressure used to advance the catheter.

In addition to biasing a catheter tip prior to insertion into the needle (10), a catheter tip can be provided that is deflected by mechanical means, such as a wire attached to one side of the tip that deflects the tip in the desired direction upon application of force to the proximal end of the deflection wire. Any device in which bending of the tip of a catheter of the invention is controlled by the physician is "actively steerable." In addition to a tip that is actively steerable by action of a wire, other methods of providing a bending force at the tip can be used, such as hydraulic pressure, electromagnetic force, or heat (such as heating a shaped memory alloy to cause it to contract). Any of a number of techniques can be used to provide selective bending of the catheter in one lateral direction.

In another embodiment, the needle (10) of this invention may be employed for intrathecal administration of nedications. The needle (10) may be used to introduce medications directly, or the needle (10) may be used as an introducer to place an intrathecal catheter. In another embodiment, the needle (10) may be used as a shunt device, or to implant a shunt device to monitor cerebrospinal fluid pressures.

In another embodiment, the needle (10) may be used as an introducer for one or more tools to perform percutaneous cordotomies. This procedure involves advancing the needle (10) into or past the intrathecal space and selectively destroying and/or disabling one or more parts of the spinal cord.

In another embodiment, the needle (10) may be used as an introducer for tools to perform cryo-analgesic and/or radiofrequency thermo-coagulation. In this procedure, the tools are used to selectively freeze and/or burn nerves, for example the occipital nerve or a nerve root that innervates a problem joint.

In another embodiment, the needle (10) may be used as an introducer for tools to perform dorsal root ganglionectomies. In this procedure, the tools may be used to selectively destroy and/or disable nerve roots for nerves that lead to painful areas.

In another embodiment, the needle (10) may be used as an introducer for tools to perform percutaneous mechanical or laser diskectomy. In these procedures, the tools may be used to destroy and/or remove a disk.

In another embodiment, the needle (10) may be used as an introducer for tools to perform vertebroplasty. In this procedures, the needle (10) may be inserted into the bone to introduce cement or another compound to lock the bone in its current state, or a balloon catheter or other device may be used to restore the bone's height prior to introducing cement or another compound to lock the bone at its restored height.

In another embodimen, the needle (10) of this invention may be employed in any other known manner. In one embodiment, the needle (10) is used such that the longitudinal axis of the cutting surface (40) is parallel to the dura fibers (not shown) when the needle is inserted to minimize cutting of the dura fibers and post dural puncture headaches.

In one embodiment, the needle (10) has a generally circular cross-section. In another embodiment, the needle (10) has a non-circular cross-section, for example, oval, rectangular, diamond, square, triangular, etc. In one embodiment, the lumen (28) has a non-circular cross-section, for example, oval, rectangular, diamond, square, triangular, etc, where the non-circular lumen (28) is adapted to be used with a corresponding catheter or other device having a non-circular cross-section. In another embodiment, the combination of a non-circular catheter and a non-circular lumen may be used to guide the catheter within a patient's body.

In one embodiment, the needle (10) has a size from about 8 to about 20 gauge. In another embodiment, the needle (10) has a size from about 10 to about 16 gauge. In another embodiment, the needle (10) has a size from about 12 to about 14 gauge.

It will be appreciated that various changes may be made with out departing from the spirit of the present invention, the scope of which will be defined in the appended claims.

It is also contemplated the present invention may useful as a split needle wherein the needle may be removed from a catheter or other device by splitting it along the shaft (12) instead of having to slide it over the catheter. This would permit the proximal end of the catheter to be permanently secured to an adapter.

In one embodiment, needle (10) is part of a kit (not shown) that may include a spinal needle, a catheter assembly, a hub, and/or a stylet to occlude the lumen (28) of the needle (10) and placed in a package (not shown). The kit (not shown) also may include a stylet for spinal needle. The kit (not shown) also may include other items in addition to spinal needle and stylet, such as surgical tools, cameras, television monitors, lasers, guide wires, steering mechanisms, gloves, skin preparation materials, medicaments and the like for particular applications.

In one embodiment, a package (not shown) for the kit or elements of the kit may be formed from materials that are substantially resistant to microorganisms, sealed and exposed to conditions suitable to render any microorganisms therein non-viable. Suitable materials for forming the package (not shown) include but are not limited to thermoplastic films, metallic foils, paper, non-wovens as well as combinations of these materials. Suitable conditions for rendering microorganisms non-viable include, but are not limited to, exposure to gaseous agents such as ethylene oxide, vapor phase hydrogen peroxide and the like, and exposure to ionizing radiation such as is generated by electron beam, ultraviolet or gamma radiation.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. In a needle comprising a hollow shaft having opposed distal and proximal ends, the distal end having a cutting surface for insertion into a patient, the needle shaft having a lumen extending from the proximal end of the needle shaft and terminating at an opening on the top of the distal end of the needle shaft;

the improvement comprising the cutting surface, wherein the cutting surface comprises a sharpened edge and extends along a portion of the bottom of the distal end of the hollow shaft.

2. The needle of claim 1 wherein the cutting surface is from the bottom of the distal end of the hollow shaft to the front of the distal end of the hollow shaft.

3. The needle of claim 1 wherein the needle is to be used where the cutting surface is substantially parallel to dural fibers of a patient, so as minimize dura cutting and post dural puncture headaches.

4. The needle of claim 1 wherein the needle includes a needle tip, and the sharpness of the cutting surface, as measured by the grams of force required for the needle tip to puncture a sheet of two mil thick polyethylene, is from about 85 grams of force to about 125 grams of force.

5. The needle of claim 1, wherein the needle is to be used in a procedure selected from the group consisting of introducing a spinal cord stimulator, introducing a dorsal column stimulator, introducing a catheter into the epidural space for depositing medications, introducing a catheter into the neural foramen for depositing medications, introducing a catheter into the epidural space for mechanical lysis of adhesions, introducing a catheter into the epidural space for chemical lysis of adhesions, introducing at least one tool into the epidural space for an epiduroscopy, introducing at least one tool into a disk for intradiscal therapy, introducing a medication into the intrathecal space, introducing a catheter into the intrathecal space, introducing a catheter into the epidural space for chemical lysis of adhesions, introducing at least one tool into the intrathecal space for a percutaneous cordotomy, introducing at least one tool for a cryo-analgesic thermo-coagulation, introducing at least one tool for a radio-frequency thermo-coagulation, introducing at least one tool for a dorsal root ganglionectomy, introducing at least one tool for a percutaneous laser diskectomy, and introducing at least one tool for a vertebroplasty.

6. The needle of claim 1, wherein the needle is used in a procedure selected from the group consisting of introducing a spinal cord stimulator, introducing a dorsal column stimulator, introducing a catheter into the epidural space for depositing medications, introducing a catheter into the neural foramen for depositing medications, introducing a catheter into the epidural space for mechanical lysis of adhesions, introducing a catheter into the epidural space for chemical lysis of adhesions, introducing at least one tool into the epidural space for an epiduroscopy, introducing at least one tool into a disk for intradiscal therapy, introducing a medication into the intrathecal space, introducing a catheter into the intrathecal space, introducing at least one tool into the intrathecal space for a percutaneous cordotomy, introducing at least one tool for a cryo-analgesic thermo-coagulation, introducing at least one tool for a radio-frequency thermo-coagulation, introducing at least one tool for a dorsal root ganglionectomy, introducing at least one tool for a percutaneous laser diskectomy, and introducing at least one tool for a vertebroplasty.

7. The needle of claim 1 wherein the needle is from about 12 gauge to about 16 gauge.

8. A needle comprising:
   a hollow shaft having opposed distal and proximal ends, the hollow shaft having a lumen extending from the proximal end of the shaft and terminating at an opening on a top of and proximal to the distal end of the needle shaft; and
   a cutting surface at the distal end of the hollow shaft to be inserted into a patient, wherein the cutting surface comprises a sharpened edge and extends along a portion of the bottom of the distal end of the hollow shaft.

9. The needle of claim 8 wherein the cutting surface begins on the bottom of the distal end of the hollow shaft and ends on the front of the distal end of the hollow shaft.

10. The needle of claim 8 further comprising:
    a solid rod having opposed proximal and distal ends, the distance between the opposed ends of the solid rod being substantially the same as the distance between the proximal end of an adapter attached to the needle and the distal tip of the needle shaft, the proximal end of the solid rod being secured to a gripping means for holding the rod, the rod being insertable through the proximal end of the adapter such that when the gripping means abuts the proximal end of the adapter, the distal end of the rod extends within the opening in the needle shaft, wherein the rod is adapted to prevent tissue debris from clogging the lumen during introduction of the needle into a patient's body.

11. The needle of claim 8, wherein the needle is to be used in a procedure selected from the group consisting of introducing a spinal cord stimulator, introducing a dorsal column stimulator, introducing a catheter into the epidural space for depositing medications, introducing a catheter into the neural foramen for depositing medications, introducing a catheter into the epidural space for mechanical lysis of adhesions, introducing a catheter into the epidural space for chemical lysis of adhesions, introducing at least one tool into the epidural space for an epiduroscopy, introducing at least one tool into a disk for intradiscal therapy, introducing a medication into the intrathecal space, introducing a catheter into the intrathecal space, introducing at least one tool into the intrathecal space for a percutaneous cordotomy, introducing at least one tool for a cryo-analgesic thermocoagulation, introducing at least one tool for a radiofrequency thermo-coagulation, introducing at least one tool for a dorsal root ganglionectomy, introducing at least one tool for a percutaneous laser diskectomy, and introducing at least one tool for a vertebroplasty.

12. The needle of claim 8, wherein the needle is used in a procedure selected from the group consisting of introducing a spinal cord stimulator, introducing a dorsal column stimulator, introducing a catheter into the epidural space for depositing medications, introducing a catheter into the neural foramen for depositing medications, introducing a catheter into the epidural space for mechanical lysis of adhesions, introducing a catheter into the epidural space for chemical lysis of adhesions, introducing at least one tool into the epidural space for an epiduroscopy, introducing at least one tool into a disk for intradiscal therapy, introducing a medication into the intrathecal space, introducing a catheter into the intrathecal space, introducing at least one tool into the intrathecal space for a percutaneous cordotomy, introducing at least one tool for a cryo-analgesic thermocoagulation, introducing at least one tool for a radiofrequency thermo-coagulation, introducing at least one tool for a dorsal root ganglionectomy, introducing at least one tool for a percutaneous laser diskectomy, and introducing at least one tool for a vertebroplasty.

13. The needle of claim 8 further comprising a beveled surface, wherein the beveled surface is rounded and extends from the distal end of the cutting surface on the bottom of the shaft to the opening of the lumen on the top of the shaft.

14. The needle of claim 13 wherein the beveled surface has a radial length less than about 25% of the needle outside diameter.

15. The needle of claim 8 wherein the cutting surface has the shape of a hull and extends from the outer edge of the bottom of the needle shaft to the front of the distal end of the shaft.

16. A method of installing a catheter in an epidural space of a patient comprising:
    (a) providing a needle comprising a hollow shaft having opposed distal and proximal ends, the distal end having a cutting surface for insertion into a patient, the needle shaft having a lumen extending from the proximal end of the needle shaft and terminating at an opening on the top of the distal end of the needle shaft, wherein the cutting surface comprises a sharpened edge and extends along a portion of the bottom of the distal end of the hollow shaft;
    (b) pushing a needle into the epidural space with a cutting surface of the needle substantially parallel to dura fibers of the patient, wherein the needle comprises a substantially straight cutting surface;
    (c) feeding a catheter through the needle and into the epidural space;
    (d) removing the needle, while holding the catheter stationary; and
    (e) securing the catheter.

17. A needle kit comprising:
    a needle;
    a lumen through the needle having a end on a top surface of a distal end of the needle;
    a stylet to fit inside the lumen of the needle;
    a catheter to fit inside the lumen of the needle; and
    a hub to connect to a proximal end of the needle;
    the improvement comprising a cutting surface on the needle, wherein the cutting surface comprises a sharpened edge and extends along a portion of a bottom surface of the distal end of the needle.

18. The needle kit of claim 17 further comprising a viewing apparatus, the viewing apparatus comprising a camera to fit inside the lumen of the needle and a monitor to receive and show an output from the camera.

19. The needle kit of claim 17, wherein the needle is to be used in a procedure selected from the group consisting of introducing a spinal cord stimulator, introducing a dorsal column stimulator, introducing a catheter into the epidural space for depositing medications, introducing a catheter into the neural foramen for depositing medications, introducing a catheter into the epidural space for mechanical lysis of adhesions, introducing a catheter into the epidural space for chemical lysis of adhesions, introducing at least one tool into the epidural space for an epiduroscopy, introducing at least one tool into a disk for intradiscal therapy, introducing a medication into the intrathecal space, introducing a catheter into the intrathecal space, introducing at least one tool into the intrathecal space for a percutaneous cordotomy, introducing at least one tool for a cryo-analgesic thermocoagulation, introducing at least one tool for a radio-frequency thermo-coagulation, introducing at least one tool for a dorsal root ganglionectomy, introducing at least one tool for a percutaneous laser diskectomy, and introducing at least one tool for a vertebroplasty.

20. The needle kit of claim 17, wherein the needle is used in a procedure selected from the group consisting of introducing a spinal cord stimulator, introducing a dorsal column stimulator, introducing a catheter into the epidural space for depositing medications, introducing a catheter into the neural foramen for depositing medications, introducing a catheter into the epidural space for mechanical lysis of adhesions, introducing a catheter into the epidural space for chemical lysis of adhesions, introducing at least one tool into the epidural space for an epiduroscopy, introducing at least one tool into a disk for intradiscal therapy, introducing a medication into the intrathecal space, introducing a catheter into the intrathecal space, introducing at least one tool into the intrathecal space for a percutaneous cordotomy, introducing at least one tool for a cryo-analgesic thermo-coagulation, introducing at least one tool for a radio-frequency thermo-coagulation, introducing at least one tool for a dorsal root ganglionectomy, introducing at least one tool for a percutaneous laser diskectomy, and introducing at least one tool for a vertebroplasty.

21. A needle kit comprising:

a needle;

a lumen through the needle having a end on a top surface of a distal end of the needle;

a stylet adapted to fit inside the lumen of the needle;

a catheter adapted to fit inside the lumen of the needle; and a hub adapted to connect to a proximal end of the needle;

the improvement comprising a cutting surface on the needle, wherein the cutting surface is on a bottom surface of the distal end of the needle; and a spinal needle adapted to fit inside the lumen of the needle.

* * * * *